(12) United States Patent
Nakanishi et al.

(10) Patent No.: US 8,906,302 B2
(45) Date of Patent: Dec. 9, 2014

(54) REAGENT PREPARING DEVICE, SPECIMEN MEASURING DEVICE AND REAGENT PREPARING METHOD

(75) Inventors: Noriyuki Nakanishi, Kakogawa (JP); Koichi Okubo, Kobe (JP); Masahiko Oguro, Kobe (JP); Tomoyuki Asahara, Kobe (JP)

(73) Assignee: Sysmex Corporation (JP)

( * ) Notice: Subject to any disclaimer, the term of this patent is extended or adjusted under 35 U.S.C. 154(b) by 697 days.

(21) Appl. No.: 12/711,640

(22) Filed: Feb. 24, 2010

(65) Prior Publication Data

US 2010/0216223 A1 Aug. 26, 2010

(30) Foreign Application Priority Data

Feb. 26, 2009 (JP) ................................. 2009-044099

(51) Int. Cl.
*G01N 35/00* (2006.01)
*G01N 35/10* (2006.01)

(52) U.S. Cl.
CPC ............... *G01N 35/00663* (2013.01); *G01N 2035/00544* (2013.01); *G01N 35/1002* (2013.01); *G01N 2035/00673* (2013.01)
USPC ........... 422/63; 435/287.3; 366/132; 436/179

(58) Field of Classification Search
CPC ............... G01N 35/1002; G01N 2035/00544; G01N 35/00663; G01N 2035/00673
See application file for complete search history.

(56) References Cited

U.S. PATENT DOCUMENTS

| 5,800,056 | A | 9/1998 | Suzuki et al. |
| 5,821,127 | A | 10/1998 | Akai et al. |
| 2005/0013739 | A1 | 1/2005 | Dupont et al. |
| 2006/0201857 | A1* | 9/2006 | Lin ................................ 210/85 |
| 2007/0118294 | A1 | 5/2007 | Jacobs |
| 2007/0212261 | A1 | 9/2007 | Tanaka et al. |
| 2008/0071503 | A1* | 3/2008 | Fujita et al. .................... 702/188 |
| 2011/0223077 | A1 | 9/2011 | Tanaka et al. |

FOREIGN PATENT DOCUMENTS

| JP | 09-104683 | A | | 4/1997 |
| JP | 2000-126767 | A | | 5/2000 |
| JP | 2007-240430 | A | | 9/2007 |
| JP | 2009-025174 | A | | 2/2009 |
| WO | WO 2009/026919 | | * | 3/2009 |
| WO | WO 2009/031461 | A1 | | 3/2009 |

\* cited by examiner

*Primary Examiner* — P. Kathryn Wright
(74) *Attorney, Agent, or Firm* — Brinks Gilson & Lione

(57) ABSTRACT

A reagent preparing device for preparing a reagent to be supplied to a measurement device for measuring a specimen, comprising: a first liquid storage unit for storing a first liquid; a reagent storage unit for storing a prepared reagent, including the first liquid and a second liquid different from the first liquid; a first liquid discarding unit for discarding the first liquid stored in the first liquid storage unit; and a controller configured for measuring an accumulated time of the first liquid in the first liquid storage unit; and controlling the first liquid discarding unit to discard the first liquid stored in the first liquid storage unit when the accumulated time reaches a predetermined time is disclosed. A specimen measuring device and a reagent preparing method are also disclosed.

17 Claims, 22 Drawing Sheets

REAGENT PREPARING DEVICE, SPECIMEN MEASURING DEVICE AND REAGENT PREPARING METHOD

RELATED APPLICATIONS

This application claims priority under 35 U.S.C. §119 to Japanese Patent Application No. JP2009-044099 filed on Feb. 26, 2009, the entire content of which is hereby incorporated by reference.

BACKGROUND OF THE INVENTION

The present invention relates to a reagent preparing device, a specimen measuring device, and a reagent preparing method capable of preparing a reagent from a plurality of different liquids.

FIELD OF THE INVENTION

A reagent preparing device capable of preparing the reagent from a plurality of different liquids is conventionally known (see e.g., U.S. Pat. No. 5,800,056).

U.S. Pat. No. 5,800,056 discloses a reagent preparing device including a reagent constant-rate tank for storing a high concentration reagent, a pure water constant-rate tank for storing pure water, and a stirring tank for stirring and mixing the high concentration reagent and the pure water. The reagent preparing device is configured to store a predetermined amount of pure water in advance in the pure water constant-rate tank. The reagent then can be rapidly prepared using the pure water stored in advance when a need to supply the reagent to a measurement section arises.

A system capable of purifying the purified water used in an analysis module is also conventionally known (see e.g., US Patent Publication No. 2005-013739).

US Patent Publication No. 2005-013739 discloses a system including a purifying module for purifying the purified water, and an analysis module for performing the analysis using the purified water. This system is configured to transfer the purified water purified by the purifying module to the analysis module immediately after the purification.

However, in the reagent preparing device described in U.S. Pat. No. 5,800,056, the reagent can be rapidly prepared, but the quality of the pure water may degrade due to generation of bacteria in the pure water in the pure water constant-rate tank when the storage time becomes long since a predetermined amount of pure water is stored in the tank in advance. Thus, if the prepared reagent is not supplied to the measurement section for a long time, the reagent with degraded quality might be prepared due to the use of the pure water with degraded quality.

In the system described in US Patent Publication No. 2005-013739, the purified water is transferred to the analysis module immediately after the purification, different from the U.S. Pat. No. 5,800,056, and thus the degradation of the quality of the purified water can be suppressed. When the purified water is required in the analysis module, there is a need to start from the stage of purifying the purified water, and thus a drawback in that the purified water cannot be rapidly supplied to the analysis module arises. Therefore, when such system is applied to preparing the reagent using the purified water, the reagent cannot be rapidly prepared since the purified water cannot be rapidly supplied.

SUMMARY OF THE INVENTION

The scope of the present invention is defined solely by the appended claims, and is not affected to any degree by the statements within this summary.

A first aspect of the present invention is a reagent preparing device for preparing a reagent to be supplied to a measurement device for measuring a specimen, comprising: a first liquid storage unit for storing a first liquid; a reagent storage unit for storing a prepared reagent, including the first liquid and a second liquid different from the first liquid; a first liquid discarding unit for discarding the first liquid stored in the first liquid storage unit; and a controller configured for measuring an accumulated time of the first liquid in the first liquid storage unit; and controlling the first liquid discarding unit to discard the first liquid stored in the first liquid storage unit when the accumulated time reaches a predetermined time.

A second aspect of the present invention is a specimen measuring device comprising: a reagent preparing unit comprising: a first liquid storage unit for storing a first liquid, a reagent storage unit for storing a prepared reagent including the first liquid and a second liquid different from the first liquid, and a first liquid discarding unit for discarding the first liquid stored in the first liquid storage unit; a controller configured for measuring an accumulated time of the first liquid in the first liquid storage unit, and controlling the first liquid discarding unit to discard the first liquid stored in the first liquid storage unit when the accumulated time reaches a predetermined time; and a measurement section for measuring a specimen using the reagent prepared by the reagent preparing unit.

A third aspect of the present invention is a reagent preparing method for preparing a reagent to be supplied to a measurement device for measuring a specimen, comprising: supplying a first liquid to a liquid storage unit; preparing a reagent including the first liquid and a second liquid different from the first liquid; measuring an accumulated time of the first liquid in the liquid storage unit; and discarding the first liquid stored in the liquid storage unit when the accumulated time reaches a predetermined time.

A fourth aspect of the present invention is a reagent preparing device for preparing a reagent to supplied to a measurement device for measuring a specimen, comprising: a first liquid storage unit for storing a first liquid; a reagent storage unit for storing a prepared reagent including the first liquid and a second liquid different from the first liquid; a first liquid discarding unit for discarding the first liquid stored in the first liquid storage unit; and a controller configured for controlling the first liquid discarding unit to discard the first liquid stored in the first liquid storage unit when accepting an instruction to terminate the operation of the reagent preparing device.

DETAILED DESCRIPTION OF THE PREFERRED EMBODIMENTS

The preferred embodiments of the present invention will be described hereinafter with reference to the drawings.

First Embodiment

First, a configuration of a reagent preparing device 4 according to a first embodiment of the present invention will be described with reference to FIGS. 1 to 14. In the first embodiment, a case of using the reagent preparing device 4 according to the first embodiment of the present invention as one part of a blood analyzer 1 for performing a blood test will be described.

Figure 1:
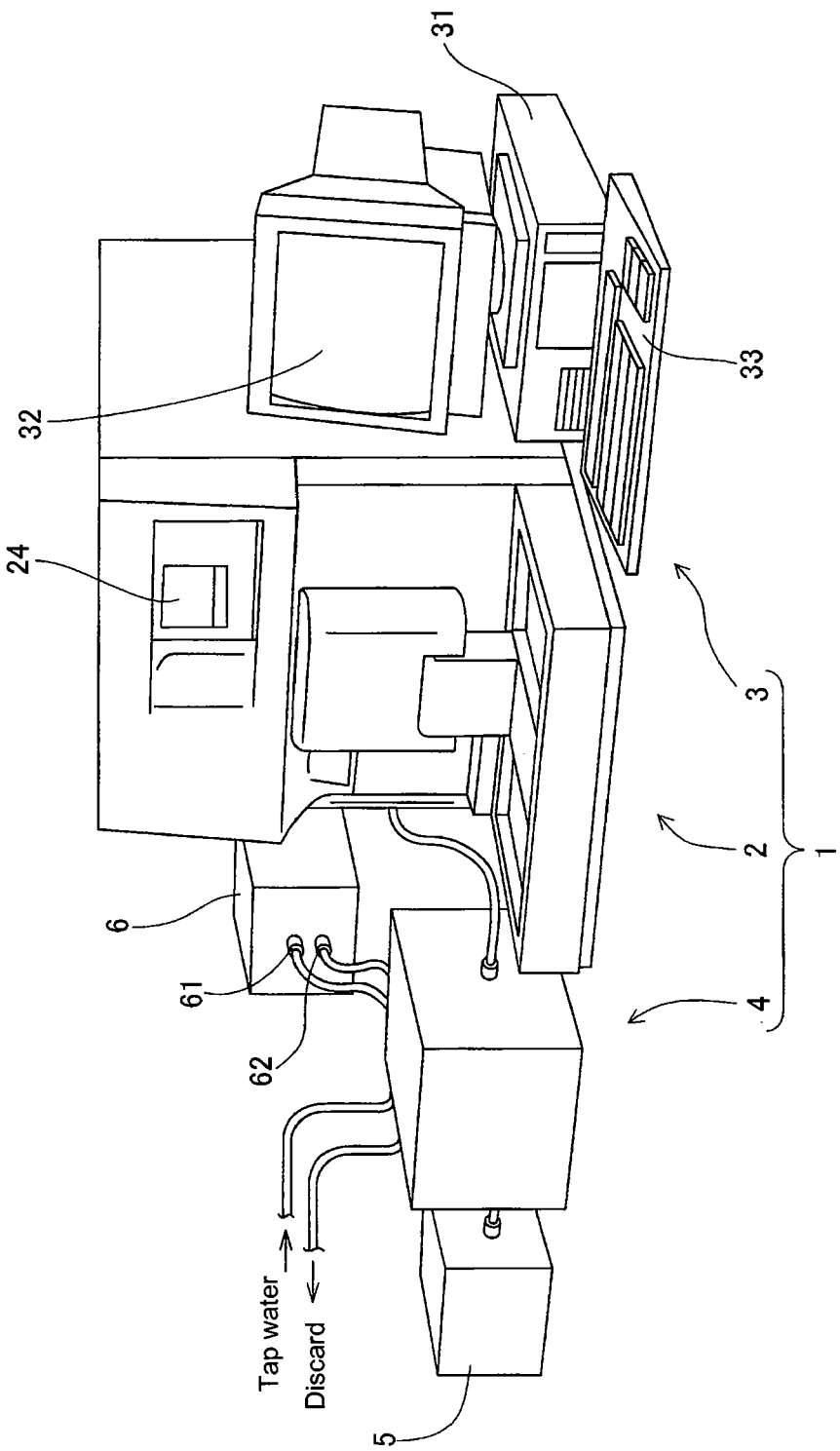
FIG. 1 is a perspective view showing a usage state of a reagent preparing device according to a first embodiment of the present invention.

As shown in FIG. 1, the blood analyzer 1 is configured by a measurement section 2 having a function of measuring the blood, a data processing section 3 for analyzing the measurement data output from the measurement section 2 and obtaining an analysis result, and the reagent preparing device 4 for preparing a reagent for use in the processing of a specimen. The measurement section 2 is configured to perform measurements on white blood cells, reticulocytes, and blood platelets in the blood through a flow cytometry method. The measurement section 2 is configured to dilute the blood using a reagent prepared and supplied by the reagent preparing device 4 and to perform measurements on white blood cells, reticulocytes, and blood platelets. The measurement section 2 is also configured to clean a sampling valve 21b, a reaction chamber 21c and the like arranged in a sample preparing unit 21, as well as a sheath flow cell 22c and the like arranged in a detection unit 22, which are to be hereinafter described, using the reagent prepared and supplied by the reagent preparing device 4 as a cleaning fluid. The flow cytometry method is a measurement method of particles (blood cells) for detecting the forward scattered light, the lateral scattered light, and the lateral fluorescence emitted by the particles (blood cells) in the measurement sample by forming a sample flow including the measurement sample and irradiating the sample flow with laser light.

Figure 2:
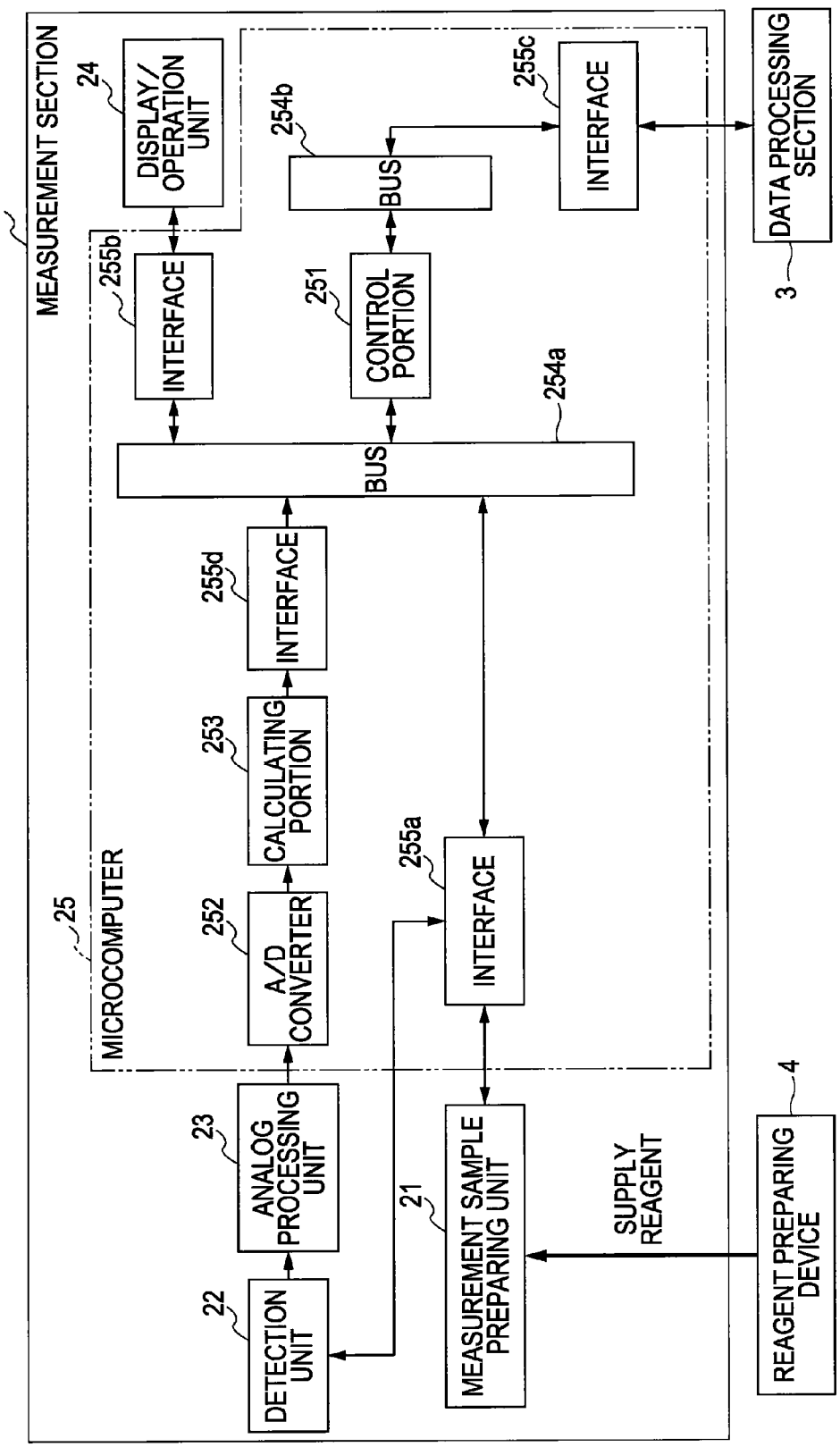
FIG. 2 is a block diagram showing a configuration of a blood analyzer including the reagent preparing device according to the first embodiment shown in FIG. 1.

As shown in FIG. 2, the measurement section 2 includes a measurement sample preparing unit 21, a detection unit 22 for performing a measurement of the measurement sample, an analog processing unit 23 with respect to the output of the detection unit 22, a display/operation unit 24, and a microcomputer 25 for controlling the measurement section 2.

Figure 3:
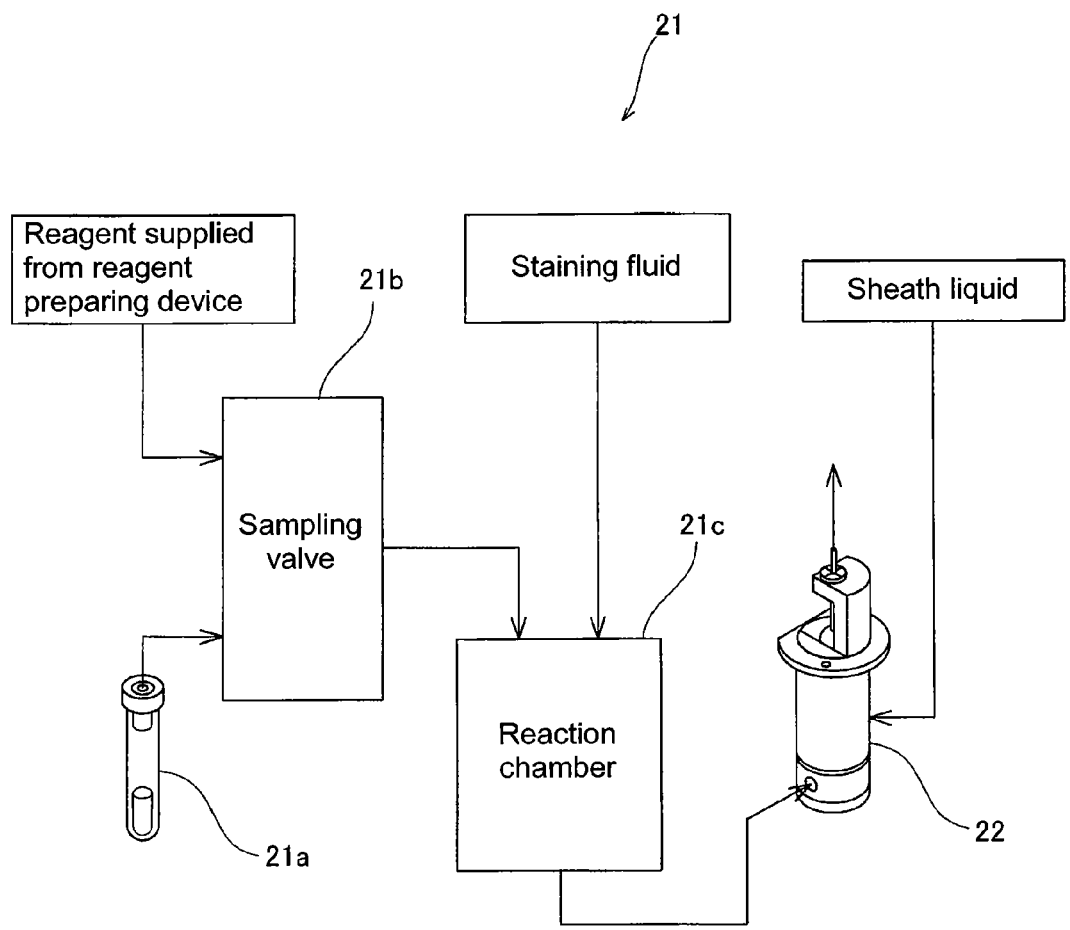
FIG. 3 is a view explaining a sample preparing unit of the blood analyzer including the reagent preparing device according to the first embodiment shown in FIG. 1.

The measurement sample preparing unit 21 is arranged to prepare a white blood cell measurement sample, a reticulocyte measurement sample, and a blood platelet measurement sample. As shown in FIG. 3, the measurement sample preparing unit 21 includes the sampling valve 21b for aspirating blood and the reaction chamber 21c. A blood collecting tube 21a stores the blood to be analyzed.

The sampling valve 21b has a function of quantifying the blood of the blood collecting tube 21a aspirated by an aspiration pipette (not shown) by a predetermined amount. The sampling valve 21b is configured so that a predetermined reagent can be mixed with the aspirated blood. That is, the sampling valve 21b is configured so that a diluted sample in which a predetermined amount of reagent supplied from the reagent preparing device 4 is mixed in a predetermined amount of blood can be generated.

The reaction chamber 21c is configured so that a predetermined staining fluid is further mixed to the diluted sample supplied from the sampling valve 21b and reacts with it for a predetermined time. The measurement sample preparing unit 21 thus has a function of preparing the white blood cell measurement sample in which the white blood cells are stained and the red blood cells are hemolyzed. The measurement sample preparing unit 21 also has a function of preparing the reticulocyte measurement sample in which the reticulocyte is stained and a function of preparing the blood platelet measurement sample in which the blood platelet is stained.

The measurement sample preparing unit 21 is also configured to supply the white blood cell measurement sample with the sheath liquid from the measurement sample preparing unit 21 to the sheath flow cell 22c described later (see FIG. 4) at the time of a white blood cell differential measurement (hereinafter also referred to as "DIFF measurement") mode.

The measurement sample preparing unit 21 is also configured to supply the reticulocyte measurement sample with the sheath liquid from the measurement sample preparing unit 21 to the sheath flow cell 22c at the time of a reticulocyte measurement (hereinafter also referred to as "RET measurement") mode. Furthermore, the measurement sample preparing unit 21 is also configured to supply the blood platelet measurement sample with the sheath liquid from the measurement sample preparing unit 21 to the sheath flow cell 22c at the time of a blood platelet measurement (hereinafter also referred to as "PLT measurement") mode.

Figure 4:
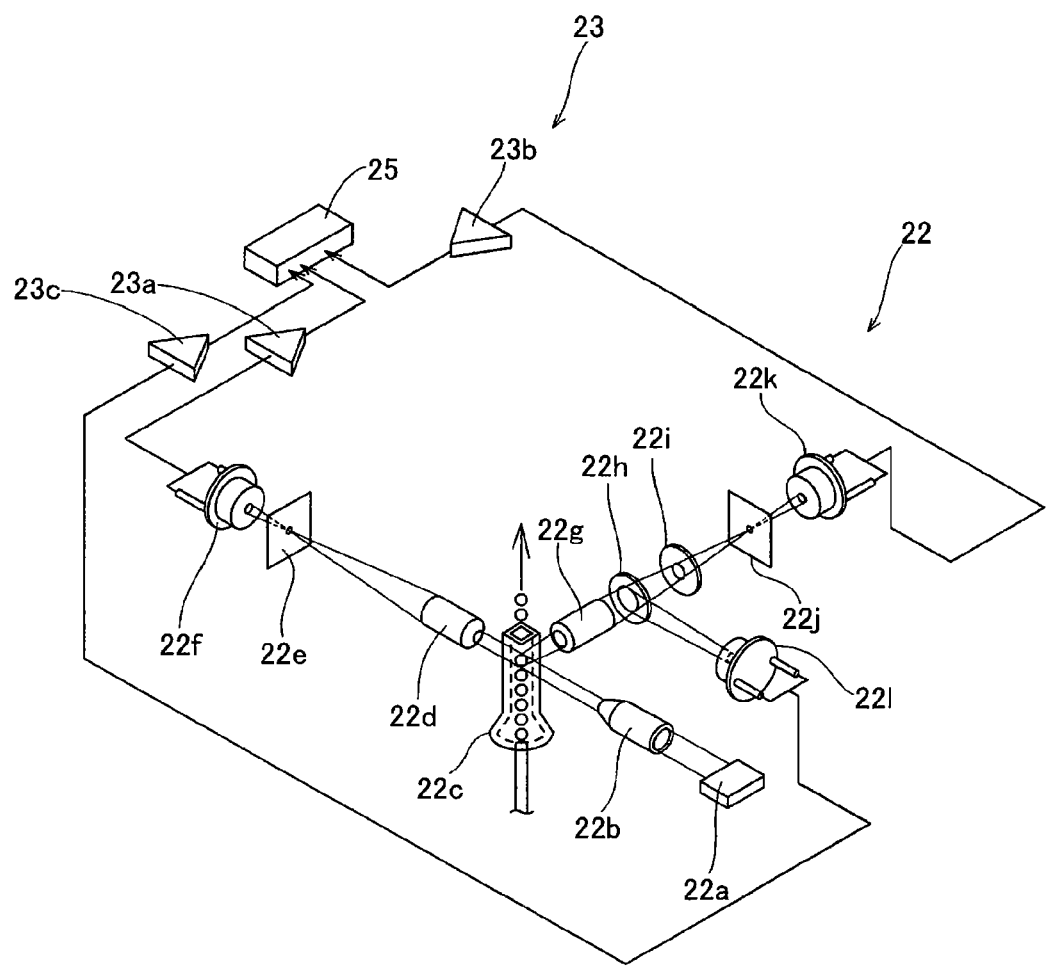
FIG. 4 is a schematic view showing a detection unit of the blood analyzer including the reagent preparing device according to the first embodiment shown in FIG. 1.

As shown in FIG. 4, the detection unit 22 includes a light emitting portion 22a for emitting laser light, an irradiation lens unit 22b, the sheath flow cell 22c irradiated with laser light, a light collecting lens 22d arranged on an extended line in a direction the laser light emitted from the light emitting portion 22a advances, a pin hole 22e and a PD (Photo Diode) 22f, a light collecting lens 22g arranged in a direction intersecting the direction the laser light emitted from the light emitting portion 22a advances, a dichroic mirror 22h, an optical filter 22i, a pin hole 22j and an APD (Avalanche Photo Diode) 22k, and a PD 22l arranged at the side of the dichroic mirror 22h.

The light emitting portion 22a is arranged to emit light to the sample flow including the measurement sample that passes the inside of the sheath flow cell 22c. The irradiation lens unit 22b is arranged to convert the light emitted from the light emitting portion 22a to parallel light. The PD 22f is arranged to receive the forward scattered light output from the sheath flow cell 22c. The information on the size of the particle (blood cell) in the measurement sample can be obtained from the forward scattered light output from the sheath flow cell 22c.

The dichroic mirror 22h is arranged to separate the lateral scattered light and the lateral fluorescence output from the sheath flow cell 22c. Specifically, the dichroic mirror 22h is arranged to have the lateral scattered light output from the sheath flow cell 22c enter to the PD 22l, and to have the lateral fluorescence output from the sheath flow cell 22c enter to the APD 22k. The PD 22l is arranged to receive the lateral scattered light. Internal information, for example, the size of the core of the particle (blood cell) in the measurement sample can be obtained from the lateral scattered light output from the sheath flow cell 22c. The APD 22k is arranged to receive the lateral fluorescence. Information on the staining degree of the particle (blood cell) in the measurement sample can be obtained from the lateral fluorescence output from the sheath flow cell 22c. The PD 22f, 22l, and the APD 22k respectively have a function of converting the received optical signal to an electrical signal.

As shown in FIG. 4, the analog processing unit 23 includes amplifiers 23a, 23b, and 23c. The amplifiers 23a, 23b, and 23c are respectively arranged to perform amplification and waveform processing on the electrical signal output from the PD 22f, 22l, and the APD 22k.

As shown in FIG. 2, the microcomputer 25 includes a control portion 251 including a control processor and a memory for operating the control processor, an A/D converter 252 for converting a signal output from the analog processing unit 23 to a digital signal, and a calculating portion 253 for performing a predetermined process on the digital signal output from the A/D converter 252.

The control portion 251 has a function of controlling the measurement sample preparing unit 21 and the detection unit 22 through a bus 254a and an interface 255a. The control portion 251 is connected with the display/operation unit 24 through the bus 254a and an interface 255b, and connected with the data processing section 3 through a bus 254b and an interface 255c. The calculating portion 253 has a function of outputting a calculation result to the control portion 251 through an interface 255d and the bus 254a. The control portion 251 has a function of transmitting the calculation result (measurement data) to the data processing section 3.

Figure 5:
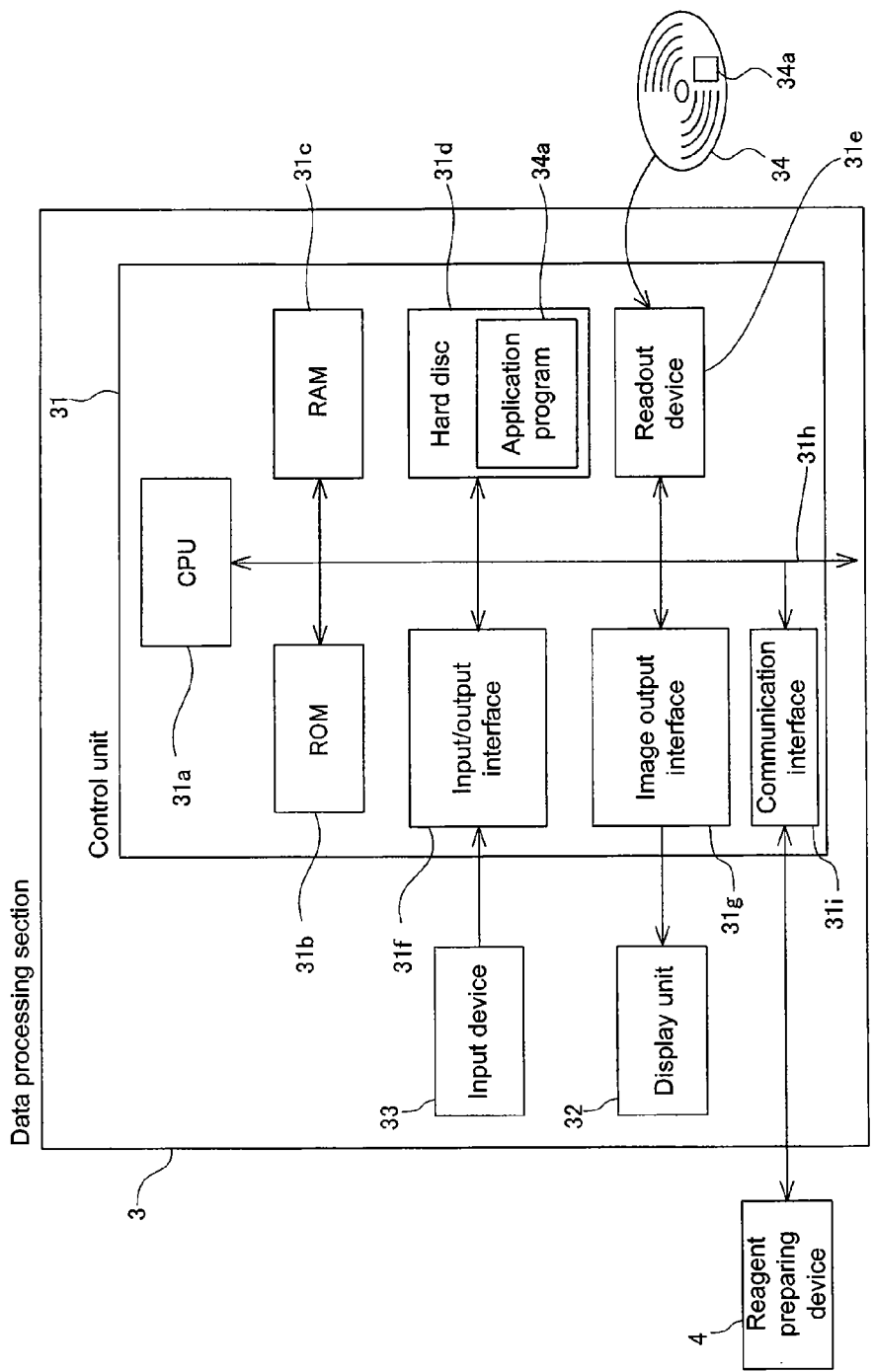
FIG. 5 is a block diagram showing a configuration of a data processing section of the blood analyzer including the reagent preparing device according to the first embodiment shown in FIG. 1.

As shown in FIG. 1, the data processing section 3 includes a personal computer (PC) and the like, and has a function of analyzing the measurement data of the measurement section 2 and displaying the analysis result. The data processing section 3 includes a control unit 31, a display unit 32, and an input device 33, as shown in FIG. 5.

The control unit 31 has a function of transmitting a measurement start signal including the measurement mode information and a shutdown signal to the measurement section 2. As shown in FIG. 5, the control unit 31 is also configured by a CPU 31a, a ROM 31b, a RAM 31c, a hard disc 31d, a readout device 31e, an input/output interface 31f, an image output interface 31g and a communication interface 31i. The CPU 31a, the ROM 31b, the RAM 31c, the hard disc 31d, the readout device 31e, the input/output interface 31f, the image output interface 31g and the communication interface 31h are connected by a bus 31i.

The CPU 31a is arranged to execute computer programs stored in the ROM 31b and the computer programs loaded in the RAM 31c. The ROM 31b is configured by mask ROM, PROM, EPROM, EEPROM, and the like, and is recorded with computer programs to be executed by the CPU 31a, data used for the same, and the like.

The RAM 31c is configured by SRAM, DRAM and the like. The RAM 31c is used to read out the computer programs recorded on the ROM 31b and the hard disc 31d. The RAM 31c is used as a work region of the CPU 31a when executing the computer programs.

The hard disc 31d is installed with various computer programs to be executed by the CPU 31a such as operating system and application program, as well as data used in executing the computer program. The application program 34a described later is also installed in the hard disc 31d.

The readout device 31e is configured by flexible disc drive, CD-ROM drive, DVD-ROM drive and the like, and is able to read out computer programs and data recorded on a portable recording medium 34. The application program 34a causing the computer to implement a predetermined function is stored in the portable recording medium 34. The computer serving as the data processing section 3 reads out the application program 34a from the portable recording medium 34, and installs the application program 34a to the hard disc 31d.

The application program 34a is not only provided by the portable recording medium 34, and may be provided through an electrical communication line (wired or wireless) from external devices communicably connected with the data processing section 3 by the electrical communication line. For instance, the application program 34a may be stored in the hard disc of the server computer on the Internet, wherein the data processing section 3 can access the server computer to download the application program 34a and install the application program 34a in the hard disc 31d.

Operating system providing graphical user interface environment such as WINDOWS® manufactured and sold by US Microsoft Co. is installed in the hard disc 31d. In the following description, the application program 34a according to the first embodiment is assumed to be operating on the operating system.

The input/output interface 31f is configured by serial interface such as USB, IEEE1394 and RS-232C; parallel interface such as SCSI, IDE and IEEE1284; analog interface such as a D/A converter and an A/D converter, and the like. The input device 33 including a keyboard and a mouse is connected to the input/output interface 31f, so that the user can input data to the data processing section 3 using the input device 33. The user can also select the measurement mode, and activate and shut down the measurement section 2 and the reagent preparing device 4 using the input device 33. For instance, when the user instructs to activate or shut down using the input device 33, an activation signal or a shut down signal is transmitted to the reagent preparing device 4 through the communication interface 31i.

The image output interface 31g is connected to the display unit 32 configured by LCD, CRT or the like, and is configured to output a video signal corresponding to the image data provided from the CPU 31a to the display unit 32. The display unit 32 displays the image (screen) according to the input video signal.

In the first embodiment, the reagent preparing device 4 is arranged to prepare the reagent to be used in the measurement sample preparing unit 21 of the measurement section 2. Specifically, the reagent preparing device 4 is configured to prepare the reagent used in blood analysis by diluting a high concentration reagent to a desired concentration using the RO water produced from the tap water. The RO water is one type of pure water and is water in which impurities are removed by being transmitted through an RO (Reverse Osmosis) membrane (reverse osmosis membrane). Other than the RO water, the pure water includes purified water, deionized water and distilled water, and is water subjected to the process of removing impurities, and the purity is not particularly limited.

Figure 6:
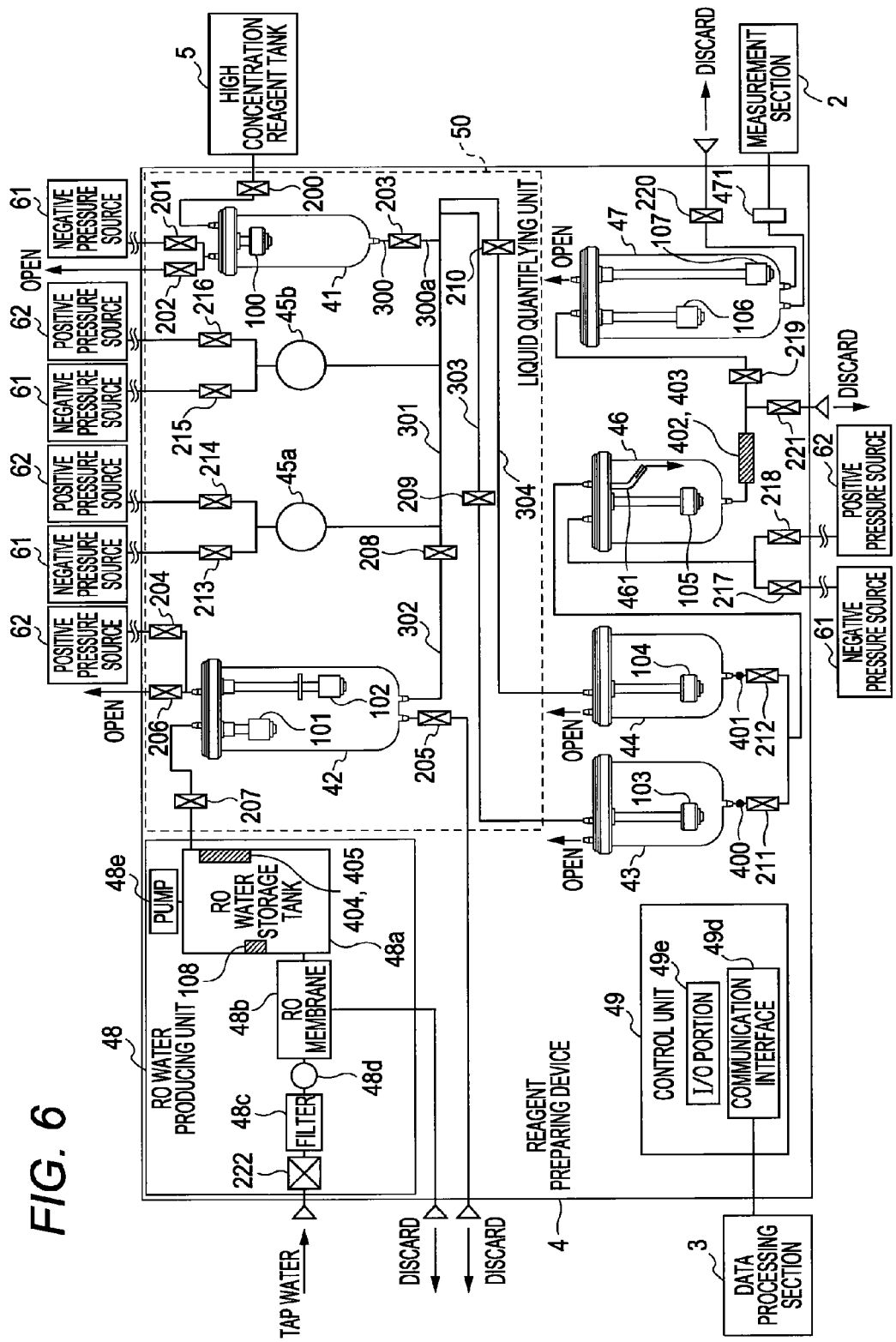
FIG. 6 is a block diagram showing a configuration of the reagent preparing device according to the first embodiment shown in FIG. 1.

As shown in FIG. 6, the reagent preparing device 4 includes a high concentration reagent chamber 41, an RO water chamber 42, two diluting chambers 43 and 44, two diaphragm pumps 45a and 45b, a stirring chamber 46, a supply chamber 47, an RO water producing unit 48, and a control unit 49 for controlling each unit of the reagent preparing device 4. The reagent preparing device 4 also includes a pneumatic unit 6 (see FIG. 1) installed at the exterior of the housing, and is configured to send each liquid in the device using negative pressure and positive pressure supplied from the pneumatic unit 6. The pneumatic unit 6 includes a negative pressure source 61 for supplying negative pressure and a positive pressure source 62 for supplying positive pressure to the reagent preparing device 4.

The high concentration reagent chamber 41 is configured to supply the high concentration reagent from a high concentration reagent tank 5. The high concentration reagent chamber 41 includes a float switch 100 for detecting that a predetermined amount of high concentration reagent is stored in the chamber. The float switch 100 is configured such that the float portion moves up and down according to the liquid amount (liquid level) in the high concentration reagent chamber 41. Each unit is controlled by the control unit 49 such that the high concentration reagent is supplied from the high concentration reagent tank 5 to the high concentration reagent chamber 41 when the float portion of the float switch 100 reaches the lower limit. Furthermore, each unit is controlled by the control unit 49 such that the supply of the high concentration reagent from the high concentration reagent tank 5 to the high concentration reagent chamber 41 is stopped when the float portion of the float switch 100 reaches the upper limit. The float switch 100 is arranged near the upper end of the high concentration reagent chamber 41, and is configured such that the float portion reaches the upper limit when about 300 mL of the high concentration reagent is stored in the high concentration reagent chamber 41. The high concentration reagent is thus supplied such that about 300 mL is stored in the high concentration reagent chamber 41 on a constant basis.

The high concentration reagent chamber 41 is connected to the high concentration reagent tank 5 through an electromagnetic valve 200, and is connected to the negative pressure source 61 of the pneumatic unit 6 through an electromagnetic valve 201. The high concentration reagent chamber 41 is also configured to be opened to atmosphere or closed by the opening and closing of the electromagnetic valve 202. The high concentration reagent chamber 41 is connected to a flow path 301 for transferring the liquid from the diaphragm pump 45a (45b) to the diluting chamber 43 (44) by the flow path 300. An electromagnetic valve 203 is arranged on the flow path 300, which electromagnetic valve 203 is arranged near the flow path 301. Specifically, the length of the flow path 300a between the electromagnetic valve 203 and the flow path 301 is set to a small length of about 15 mm. The flow path 300 (300a) connected to the high concentration reagent chamber 41 has an inner diameter of about 1.8 mm, and the flow path 301 has an inner diameter of about 4.0 mm.

In the first embodiment, the high concentration reagent contains an antiseptic agent. The antiseptic agent may be (sodium-2-pyridylthio-1-oxide), and may be an antiseptic agent in which TKM-A (manufactured by API Co.) contains (sodium-2-pyridylthio-1-oxide).

The RO water chamber 42 is configured such that the RO water for diluting the high concentration reagent is supplied from the RO water producing unit 48. The RO water is supplied to the RO water chamber 42 by opening the electromagnetic valves 206, 207, and applying positive pressure into the RO water storage tank 48a. The RO water chamber 42 includes float switches 101 and 102 for detecting that the RO water stored in the chamber has reached the upper limit amount and the lower limit amount, respectively. The float switch 101 (102) is configured such that the float portion moves up and down according to the liquid amount (liquid level) in the RO water reagent chamber 42. Each unit is controlled by the control unit 49 such that the supply of RO water from the RO water producing unit 48 to the RO water chamber 42 is stopped when the float portion of the float switch 101 reaches the position corresponding to the upper limit amount. Furthermore, each unit is controlled by the control unit 49 such that the RO water is supplied from the RO water producing unit 48 to the RO water chamber 42 when the float portion of the float switch 102 reaches the position corresponding to the lower limit amount. The float switch 101 is arranged near the upper end of the RO water chamber 42, and is configured such that the float portion reaches the position corresponding to the upper limit amount of the RO water chamber 42 when about 600 mL of the RO water is stored in the RO water chamber 42. The float switch 102 is configured such that the float portion reaches the position corresponding to the lower limit amount of the RO water chamber 42 when the RO water stored in the RO water chamber 42 reduces to about 300 mL. The RO water of greater than or equal to about 300 mL and less than or equal to about 600 mL is thus stored in the RO water chamber 42 while the reagent preparing device 4 is operating. The RO water stored in the RO water chamber 42 does not contain an antiseptic agent.

The RO water chamber 42 is configured so that the RO water in the chamber can be discarded. Specifically, the RO water chamber 42 is connected to the positive pressure source 62 through the electromagnetic valve 204 and connected to a discard flow path through the electromagnetic valve 205, so that the RO water inside is pushed out to the discard flow path by the positive pressure force by opening both electromagnetic valves 204 and 205. The RO water chamber 42 is configured to be opened to atmosphere and closed by the opening and closing of the electromagnetic valve 206. The RO water chamber 42 is connected to the RO water storage tank 48a, to be hereinafter described, of the RO water producing unit 48 through the electromagnetic valve 207. The RO water chamber 42 is connected to the diaphragm pumps 45a and 45b by the flow path 302 through the electromagnetic valve 208.

The diluting chambers 43 and 44 are respectively arranged to dilute the high concentration reagent with the RO water. As hereinafter described, the diluting chamber 43 (44) is configured to store about 300 mL of liquid (mixed solution of high concentration reagent and RO water) sent by the diaphragm pumps 45a and 45b. The diluting chamber 43 (44) includes a float switch 103 (104) for detecting that the remaining amount of the liquid (mixed solution of high concentration reagent and RO water) stored in the chamber has reached a predetermined amount. The float switch 103 (104) is configured such that the float portion moves up and down according to the liquid amount (liquid level) in the diluting chamber 43 (44). The diluting chamber 43 (44) is configured so as to be always opened to atmosphere. The diluting chamber 43 (44) is connected to the flow path 301 by the flow path 303 (304) through the electromagnetic valve 209 (210). The flow path 303 (304) has an inner diameter of about 4 mm, similar to the flow path 301. The liquid (RO water and high concentration reagent) transferred through the flow path 301 can be transferred to the diluting chamber 43 by opening the electromagnetic valve 209 with the electromagnetic valve 210 closed. The liquid (RO water and high concentration reagent) transferred through the flow path 301 can be transferred to the diluting chamber 43 by opening the electromagnetic valve 210 with the electromagnetic valve 209 closed. In other words, the electromagnetic valves 209 and 210 are respectively configured to function as a flow path switching unit of the flow paths 303 and 304.

The diluting chamber 43 (44) is connected to the stirring chamber 46 through the electromagnetic valve 211 (212). An air bubble sensor 400 (401) is arranged between the diluting chamber 43 (44) and the electromagnetic valve 211 (212). The air bubble sensor 400 (401) is a transmissive sensor, and is configured to detect air bubbles that pass the flow path. That the liquid (mixed solution of high concentration reagent and RO water) in the diluting chamber 43 (44) are all discharged can be checked by the control unit 49 when the float portion of the float switch 103 (104) reaches the lower limit and the air bubbles are detected by the air bubble sensor 400 (401). When the diluting chamber 43 (44) becomes empty (all liquid in the chamber is discharged), each unit is controlled by the control unit 49 so that the high concentration reagent and the RO water are supplied to the empty diluting chamber 43 (44).

The diaphragm pumps 45a and 45b have similar configuration with respect to each other, and are configured to perform the same operation at the same time. The diaphragm pump 45a (45b) has a function of quantifying about 6.0 mL (constant amount) of the high concentration reagent and the RO water in one quantifying operation. The diaphragm pump 45a (45b) is connected to the negative pressure source 61 through the electromagnetic valve 213 (215), and also connected to the positive pressure source 62 through the electromagnetic valve 214 (216).

The detailed configuration of the diaphragm pump 45a (45b) will now be described. In the first embodiment, the diaphragm pumps 45a and 45b have similar configuration with respect to each other, and thus the diaphragm pump 45a will be described as a representative, and the detailed description of the diaphragm pump 45b will be omitted.

Figure 7:
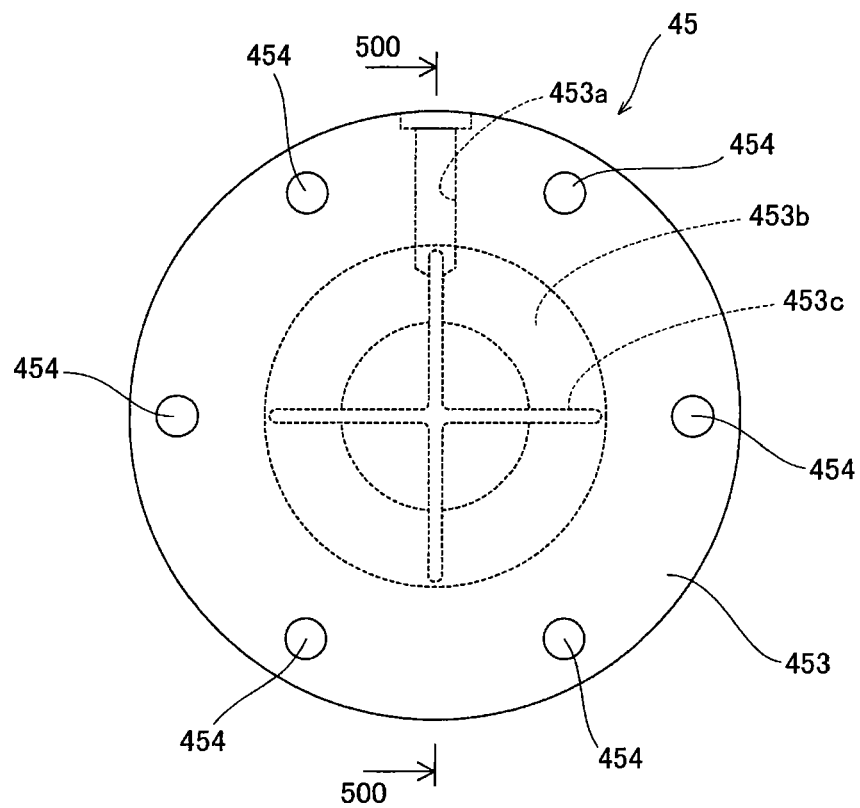
FIG. 7 is a plan view showing a diaphragm pump of the reagent preparing device according to the first embodiment shown in FIG. 1.
Figure 8:
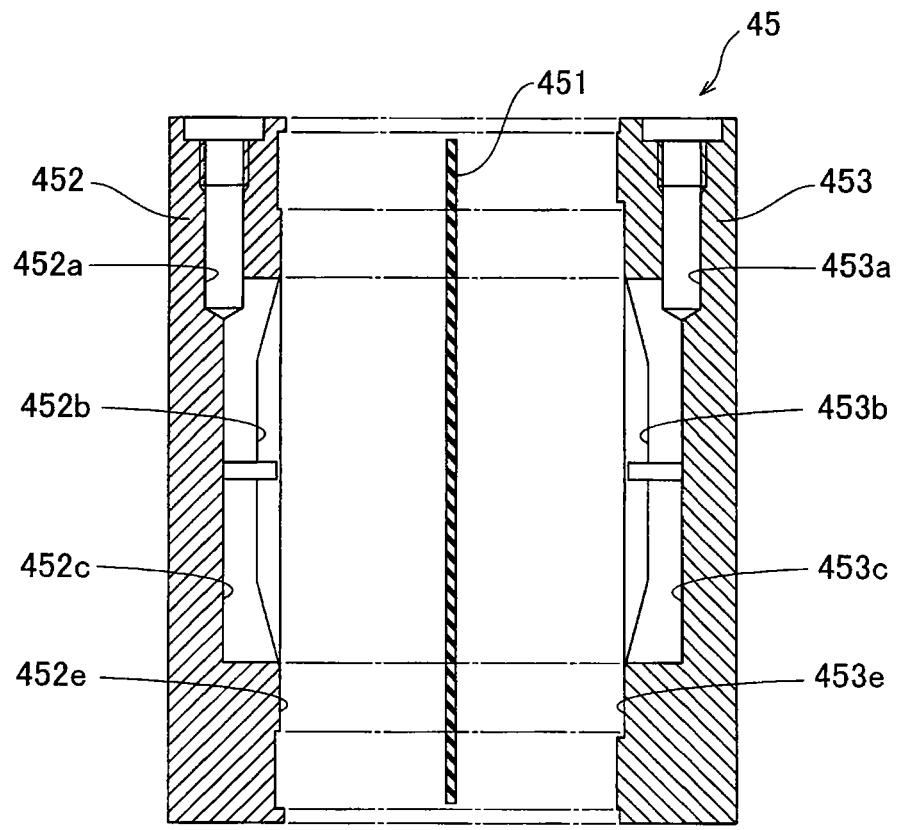
FIG. 8 is an exploded view at a cross-section taken along a line 500-500 of FIG. 7.
Figure 9:
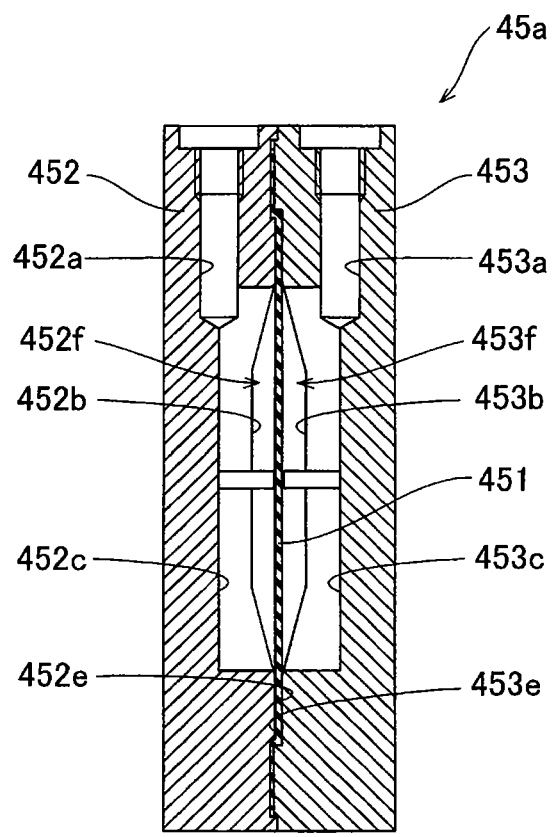
FIG. 9 is a cross-sectional view taken along the line 500-500 of FIG. 7.

As shown in FIG. 7, the diaphragm pump 45a has a circular shape in plan view. As shown in FIGS. 8 and 9, the diaphragm pump 45a includes a membrane body 451 made of rubber material such as EPDM, and a pair of case pieces 452 and 453 configured to sandwich the membrane body 451 from both sides.

Figure 10:
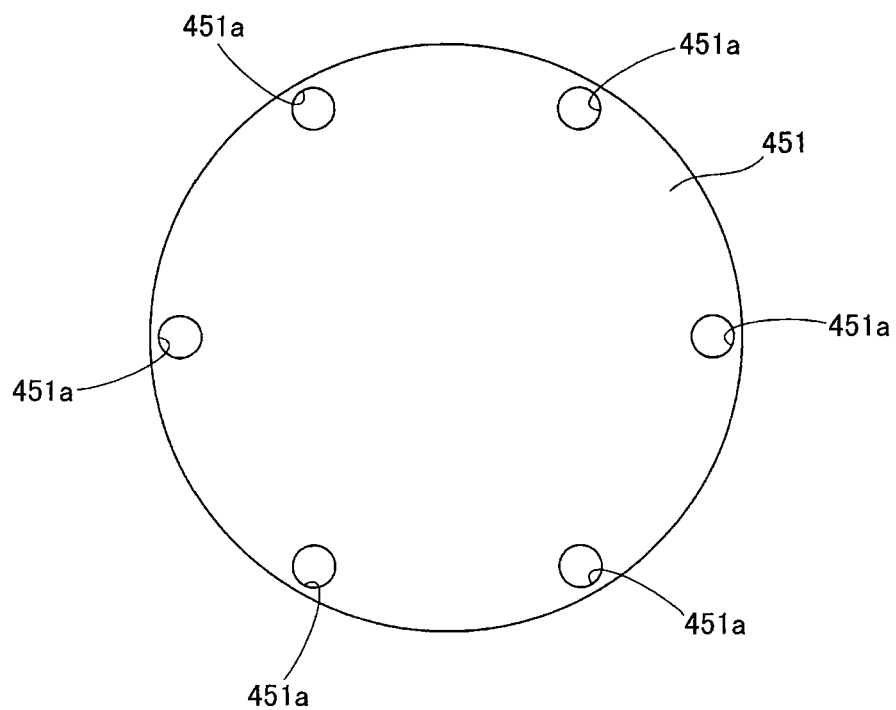
FIG. 10 is a plan view showing a membrane body of the diaphragm pump of the reagent preparing device according to the first embodiment shown in FIG. 1.

As shown in FIG. 10, the membrane body 451 is formed to a flat plate shape having a circular shape when seen in plan view, and includes six screw holes 451a for passing a screw 454. As shown in FIGS. 8 and 9, the membrane body 451 is also configured to be sandwiched by the case pieces 452 and 453 from both sides.

Figure 11:
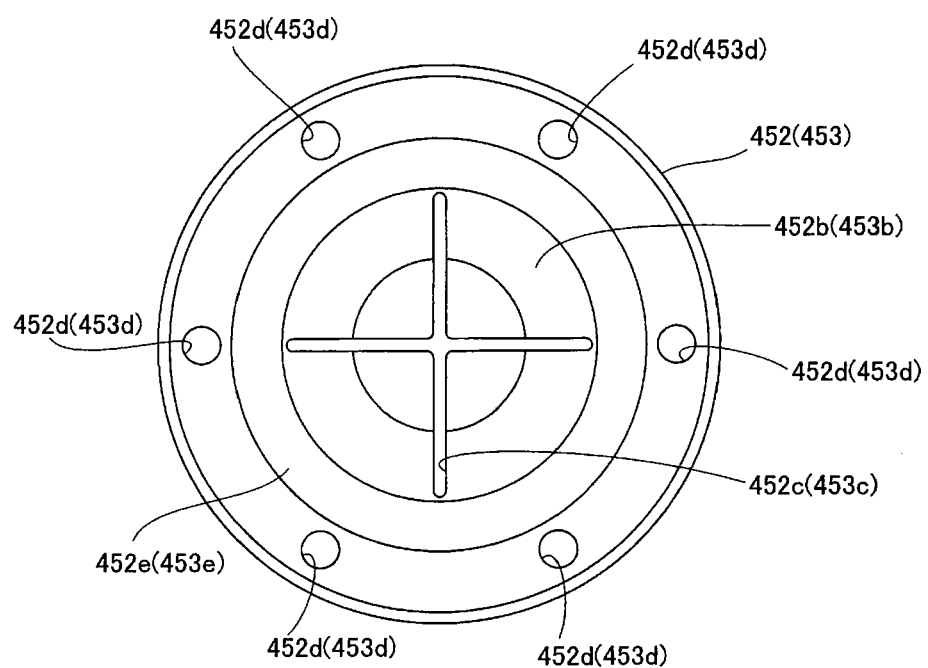
FIG. 11 is a plan view explaining an internal structure of the diaphragm pump of the reagent preparing device according to the first embodiment shown in FIG. 1.

As shown in FIGS. 8, 9, and 11, the case piece 452 includes a flow port 452a (see FIGS. 8 and 9), an inner wall 452b formed to a circular truncated cone shape, a cross-shaped groove 452c arranged at substantially the middle of the inner wall 452b when seen in plan view, six screw holes 452d (see FIG. 11), and a ring-shaped sandwiching portion 452e formed to surround the inner wall 452b when seen in plan view. As shown in FIGS. 8, 9, and 11, the case piece 453 is formed similar to the case piece 452, and a flow port 453a (see FIGS. 8 and 9), an inner wall 453b, a groove 453c, a screw hole 453d (see FIG. 11) and a sandwiching portion 453e, respectively, correspond to the flow port 452a, the inner wall 452b, the groove 452c, the screw hole 452d and the sandwiching portion 452e.

As shown in FIG. 9, the case pieces 452 and 453 are joined to each other with six screws 454 (see FIG. 7) with the membrane body 451 sandwiched with the sandwiching portions 452e and 453e. A chamber portion 452f surrounded by the inner wall 452b and the membrane body 451, and a chamber portion 453f surrounded by the inner wall 453b and the membrane body 451 are thereby formed. The flow port 452a and the chamber portion 452f are spatially connected to each other through the groove 452c, and the flow port 453a and the chamber portion 453f are spatially connected to each other through the groove 453c. The chamber portions 452f and 453f are spatially separated from each other by the membrane body 451.

Figure 12:
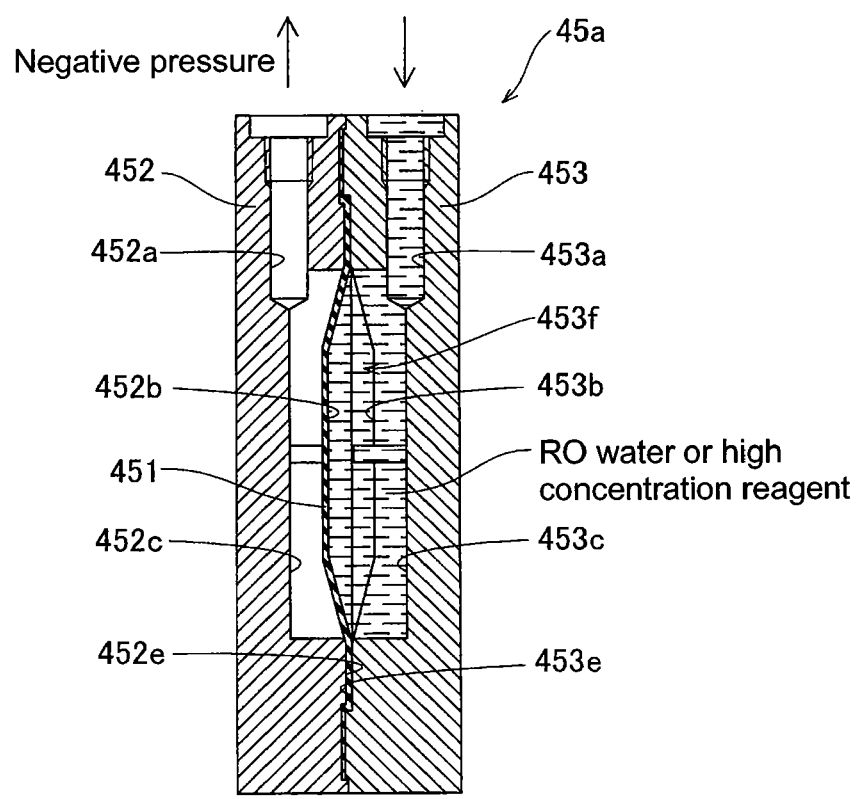
FIG. 12 is a cross-sectional view explaining a configuration of the diaphragm pump of the reagent preparing device according to the first embodiment shown in FIG. 1.
Figure 13:
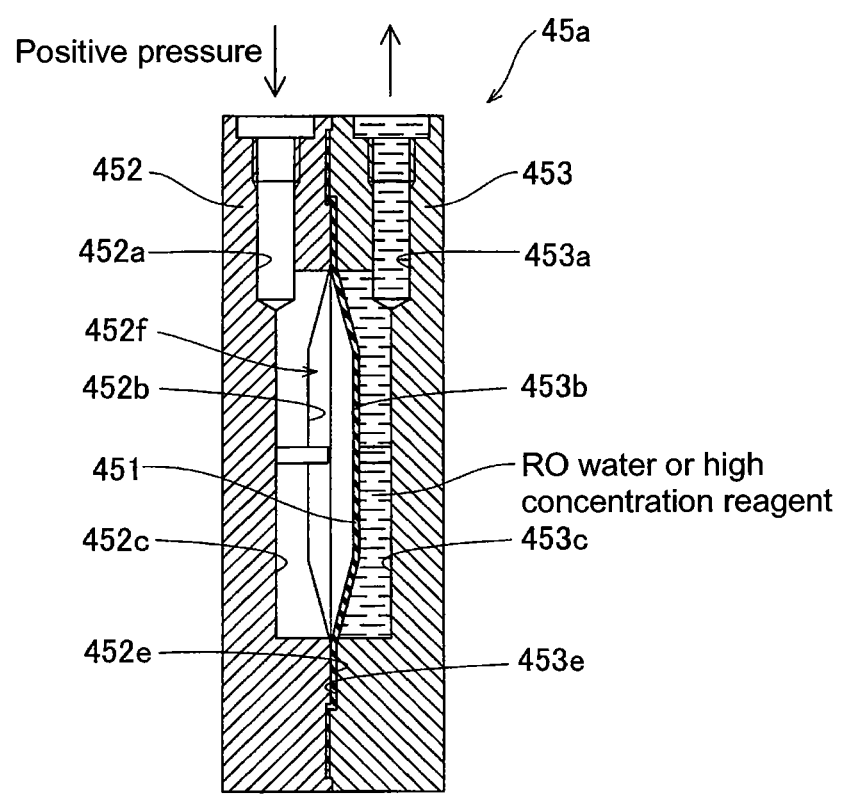
FIG. 13 is a cross-sectional view explaining a configuration of the diaphragm pump of the reagent preparing device according to the first embodiment shown in FIG. 1.

The flow port 452a is connected to the negative pressure source 61 and the positive pressure source 62. The flow port 453a is connected to the flow path 302 connected to the RO water chamber 42 and the flow path 301 for transferring liquid to the diluting chamber 43 (44). The diaphragm pump 45a is configured such that the membrane body 451 closely attaches to the inner wall 452b, as shown in FIG. 12, when the negative pressure is supplied to the chamber portion 452f by the negative pressure source 61 connected to the flow port 452a. The volume of the chamber portion 453 partitioned by the membrane body 451 is thereby enlarged, and the liquid (RO water, high concentration reagent, or mixed solution of RO water and high concentration reagent) flows into the chamber portion 453f through the flow port 453a. The diaphragm pump 45a is configured such that the membrane body 451 closely attaches to the inner wall 453b, as shown in FIG. 13, when the positive pressure is supplied to the chamber portion 452f by the positive pressure source 62 connected to the flow port 452a. The volume of the chamber portion 453f partitioned by the membrane body 451 then becomes substantially zero, and the liquid in the chamber portion 453f flows out (is pushed out) through the flow part 453a. The diaphragm pump 45a is configured so that the liquid amount that flows out in this case is about 6.0 mL. The high concentration reagent chamber 41, the RO water chamber 42, the diaphragm pumps 45a and 45b, the pneumatic unit 6, the flow paths 300 to 304, and the electromagnetic valves 200 to 210 and 213 to 216 configure the liquid quantifying unit 50 (see FIG. 6) of the reagent preparing device 4.

As shown in FIG. 6, the stirring chamber 46 is configured to accommodate about 300 mL of liquid, and is arranged to stir the liquid (mixed solution of high concentration reagent and RO water) transferred from the diluting chamber 43 (44). Specifically, the stirring chamber 46 includes a bent pipe 416, and is configured so that the liquid (mixed solution of high concentration reagent and RO water) transferred from the diluting chamber 43 (44) flows into the stirring chamber 46 along the inner wall surface of the stirring chamber 46 by passing the pipe 416. The liquid (mixed solution of high concentration reagent and RO water) transferred from the diluting chamber 43 (44) thus flows along the inner wall surface of the stirring chamber 46, whereby convention occurs and the high concentration reagent and the RO water are easily stirred. The high concentration reagent and the RO water are stirred to a certain extent in the diluting chamber 43 (44) and in the flow path from the diluting chamber 43 (44) to the stirring chamber 46, but the solution is more reliably stirred by configuring the stirring chamber 46 in the above manner.

The stirring chamber 46 includes a float switch 105 for detecting that the remaining amount of the liquid (mixed solution of high concentration reagent and RO water) accommodated in the chamber has reached a predetermined amount. The float switch 105 is configured such that the float portion moves up and down according to the liquid amount (liquid level) in the stirring chamber 46. Each unit is controlled by the control unit 49 such that about 300 mL of mixed solution is supplied from either diluting chamber 43 or 44 to the stirring chamber 46 when the float portion of the float switch 105 reaches the lower limit and the interior of the chamber becomes empty. When the mixed solution supplied from either diluting chamber 43 or 44 and stirred is discharged from the stirring chamber 46, about 300 mL of mixed solution is then supplied from the other diluting chamber 43 or 44 to the stirring chamber 46. The stirring chamber 46 is connected to the negative pressure source 61 through the electromagnetic valve 217, and connected to the positive pressure source 62 through the electromagnetic valve 218.

The supply chamber 47 is arranged to store a predetermined amount of reagent to supply to the measurement section 2. The supply chamber 47 includes a float switch 106 for detecting that the remaining amount of reagent stored in the chamber has reached about 300 mL. The supply chamber 47 also includes a float switch 107 for detecting that the remaining amount of reagent stored in the supply chamber 47 is substantially zero. The float switch 106 (107) is configured such that the float portion moves up and down according to the liquid amount (liquid level) in the supply chamber 47. The float portion of the float switch 106 is configured to be movable from the vicinity of the upper end in the height direction of the supply chamber 47 to the intermediate position. Each unit is controlled by the control unit 49 so that about 300 mL of reagent of the desired concentration is supplied from the stirring chamber 46 to the supply chamber 47 when the float portion of the float switch 106 reaches the intermediate position in the height direction of the supply chamber 47 (lower limit position in the movable range of the float portion of the float switch 106). The reagent of desired concentration of greater than or equal to about 300 mL and less than or equal to about 600 mL is stored in the supply chamber 47 on a constant basis. The reagent can be rapidly supplied to the measurement section 2 according to the supply instruction by storing a predetermined amount of reagent in the supply chamber 47. The degradation of the reagent is suppressed since the reagent contains an antiseptic agent even if the reagent is stored in the supply chamber 47.

The float portion of the float switch 107 is configured to be movable to the vicinity of the bottom of the supply chamber 47. The supply of reagent to the measurement section 2 is stopped when detected that the remaining amount of reagent accommodated in the chamber is substantially zero by the float switch 107. Therefore, the air bubbles are prevented from mixing to the reagent to be supplied to the measurement section 2 while continuing the supply of reagent to the measurement section 2 as much as possible even if the reagent is not transferred to the supply chamber 47 for some reasons.

The supply chamber 47 is connected to the stirring chamber 46 through the electromagnetic valve 219. The supply chamber 47 is configured so that the reagent in the chamber can be discarded at the time of maintenance and the like by opening the electromagnetic valve 220. The supply chamber 47 is configured so as to be opened to atmosphere on a constant basis. The supply chamber 47 is connected to the measurement section 2 through the filter 471. The filter 471 is arranged to prevent impurities from mixing in the reagent to be supplied to the measurement section 2.

A conductivity sensor 402 for measuring the electrical conductivity of the reagent is arranged between the stirring chamber 46 and the supply chamber 47. The conductivity sensor 402 includes a temperature sensor 403 for measuring the temperature of the reagent at the position where the conductivity sensor 402 is arranged. A discard flow path is connected between the conductivity sensor 402 and the electromagnetic valve 219 through the electromagnetic valve 221.

The RO water producing unit 48 is configured so that the RO water serving as the diluting liquid for diluting the high concentration reagent can be produced using tap water. The RO water producing unit 48 includes an RO water storage tank 48a, an RO membrane 48b, and a filter 48c for protecting the RO membrane 48b by removing impurities contained in the tap water. Furthermore, the RO water producing unit 48 includes a high pressure pump 48d for applying high pressure to the water passed through the filter 48c so that water molecules transmit through the RO membrane 48b, and an electromagnetic valve 222 for controlling the supply of tap water.

The RO water storage tank 48a is arranged to store the RO water transmitted through the RO film 48b. The RO water storage tank 48a includes a float switch 108 for detecting that a predetermined amount of RO water is stored. The RO water storage tank 48a includes a conductivity sensor 404 for measuring the electrical conductivity of the RO water in the RO water storage tank 48a. The conductivity sensor 404 includes a temperature sensor 405 for measuring the temperature of the RO water. The speed the RO water is supplied from the RO water producing unit 48 to the RO water storage tank 48a, that is, the production speed of the RO water by the RO water producing unit 48 is greater than or equal to about 20 L/hour and smaller than or equal to about 50 L/hour.

Figure 14:
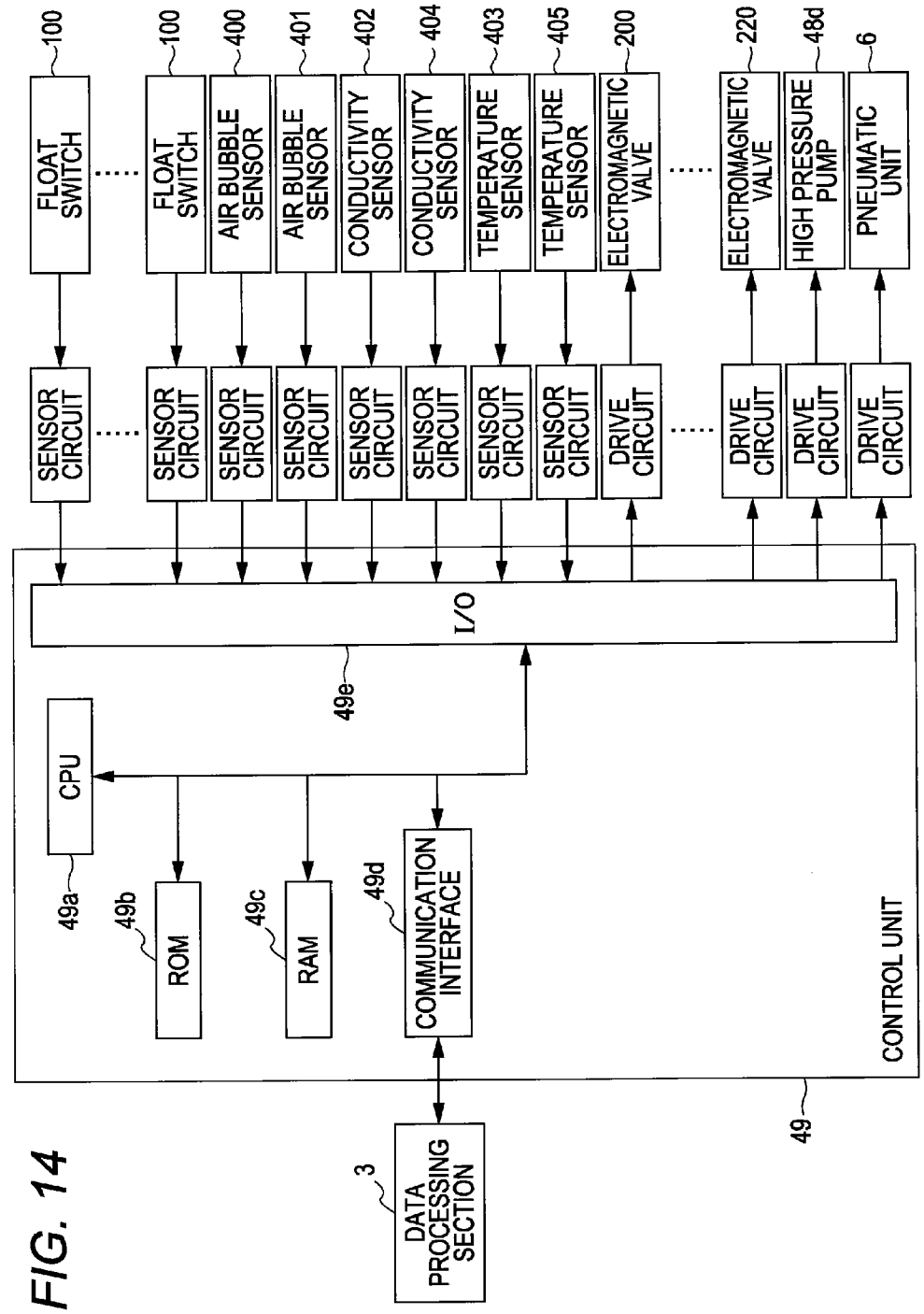
FIG. 14 is a block diagram explaining a control unit of the reagent preparing device according to the first embodiment of the present invention.

As shown in FIG. 14, the control unit 49 includes a CPU 49a, a ROM 49b, a RAM 49c, a communication interface 49d connected to the data processing section 3, and an I/O (Input/Output) portion 49e connected to each unit in the reagent preparing device 4 through each circuit.

The CPU 49a can execute computer programs stored in the ROM 49b and the computer programs loaded in the RAM 49c. The CPU 49a is configured to use the RAM 49c as a work region when executing the computer programs. A computer program for causing the CPU 49a to function as a timer is stored in the ROM 49b. The CPU 49a thus can measure (time) the elapsed time from a predetermined event.

A general formula for obtaining a target value of the electrical conductivity of the reagent is expressed with the following equation (1).

$$Z_0 = \{X + (A-1)Y\}/A \quad (1)$$

In the equation (1), $Z_0$ is, at 25° C., the target value (ms/cm) of the electrical conductivity of the reagent in which the high concentration reagent and the RO water are mixed and stirred, X is the electrical conductivity (ms/cm) of the high concentration reagent at 25° C., Y is the electrical conductivity (ms/cm) of the RO water at 25° C., and A is the diluting magnification (known) (25 times in the first embodiment). Here, X is a value unique to the high concentration reagent, and is a known value obtained through experiments and the like in advance.

The correction formula for taking into consideration the temperature of the RO water obtained by the temperature sensor 405 and the temperature of the reagent obtained by the temperature sensor 403 is expressed with the following equation (2).

$$Z = [\{X+(A-1)Y\}/A] \times \{1+\alpha1(T2-25)\} = [[X+(A-1)Y1/\{1+\alpha0(T1-25)\}]/A] \times \{1+\alpha1(T2-25)\} \quad (2)$$

In the equation (2), Z is, at T2° C., the target value (ms/cm) of the electrical conductivity of the reagent in which the high concentration reagent and the RO water are mixed and stirred, Y1 is the electrical conductivity of the RO water at T1° C., T1 is the temperature of the RO water (° C.), T2 is the temperature (° C.) of the reagent in which the high concentration reagent and the RO water are mixed and stirred, $\alpha0$ is the temperature coefficient compared with the electrical conductivity of the RO water at 25° C., and $\alpha1$ is the temperature coefficient compared with the electrical conductivity of the reagent in which the high concentration reagent and the RO water are mixed and stirred, at 25° C. The temperature coefficients $\alpha0$ and $\alpha1$ differ depending on the type and concentration of the liquid, but are 0.02 for simplification in JIS (Japanese Industrial Standards).

In the first embodiment, the CPU 49a is configured to calculate the target value Z from the equation (2). Therefore, the CPU 49a determines the target value based on the desired diluting magnification A (known), the detection value Y1 of the electrical conductivity of the RO water, the measurement value T1 of the temperature of the RO water, the measurement value T2 of the temperature of the mixed and stirred reagent, and the electrical conductivity X (known) of the high concentration reagent.

The communication interface 49d is configured to transmit error information to the data processing section 3 so that the user can check the error that occurred in the reagent preparing device 4. The error information includes information for urging replacement of the high concentration reagent tank 5, information notifying that the RO water is no longer supplied, and information notifying the abnormality of the negative pressure source 61 and the positive pressure source 62. An error notification is displayed on the display unit 32 of the data processing section 3 based on the error information.

As shown in FIG. 14, the I/O portion 49e is configured so that signals are input from the float switches 100 to 108, the air bubble sensors 400, 401, the conductivity sensors 402, 404, and the temperature sensors 403, 405 through each sensor circuit. The I/O portion 49e is configured to output signals to each drive circuit to control the drive of the electromagnetic valves 200 to 222, the high pressure pump 48d, and the pneumatic unit 6 through each drive circuit.

The RO water automatic discharge processing operation according to the first embodiment of the present invention will now be described with reference to FIGS. 6 and 15. The processes of steps S1 to S7 shown in FIG. 15 are continuously executed in parallel to the reagent preparation processing operation, to be described later using FIGS. 16 and 17, from when the reagent preparing device 4 is activated until shut down.

Figure 15:
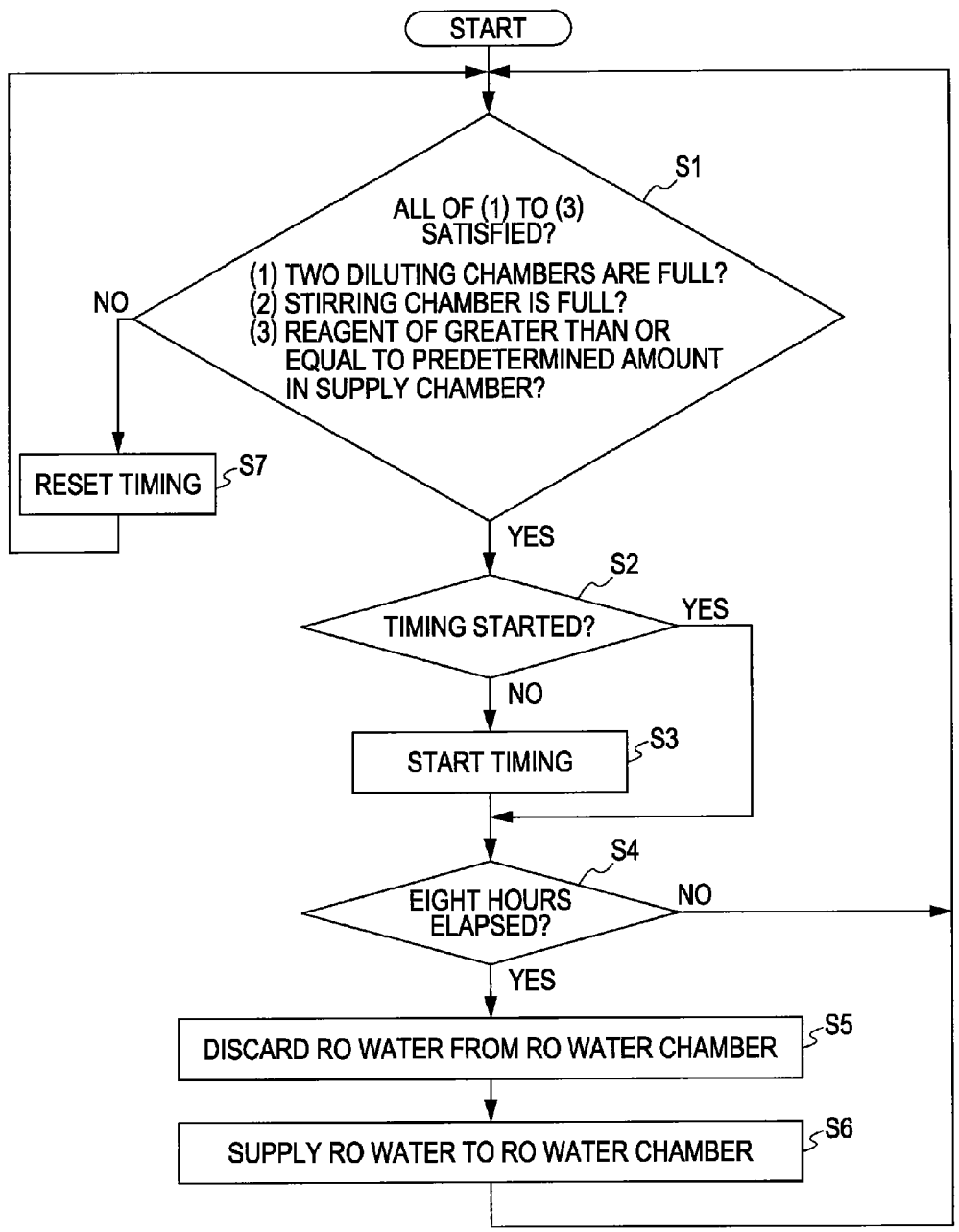
FIG. 15 is a flowchart explaining an RO water automatic discharge processing operation of the reagent preparing device according to the first embodiment of the present invention.

In the first embodiment, whether or not a predetermined condition is satisfied is determined by the CPU 49a in step S1 of FIG. 15. Specifically, whether or not the following three conditions are all satisfied is determined. The first condition is that the two diluting chambers 43 and 44 shown in FIG. 6 are both filled with about 300 mL of mixed solution; the second condition is that the stirring chamber 46 is filled with about 300 mL of mixed solution, and the third condition is that the supply chamber 47 is stored with greater than or equal to about 300 mL and less than or equal to about 600 mL of reagent of the desired concentration. If all three conditions are satisfied, a new reagent preparation process is not required, and thus the RO water is accumulated in the RO water chamber 42 without the RO water in the RO water chamber 42 being used. In other words, whether or not the RO water in the RO water chamber 42 is no longer used (no necessity to prepare reagent) can be determined by determining whether or not all three conditions are satisfied by the CPU 49a.

If all three conditions are satisfied (i.e., RO water in RO water chamber 42 is no longer used), whether or not timing is started is determined by the CPU 49a in step S2, and the process proceeds to step S4 if timing is already started. If timing is not started, the timing is started in step S3. Thereafter, in step S4, whether or not eight hours have elapsed from the start of timing is determined, and the process returns to step S1 if eight hours have not elapsed.

If eight hours have elapsed from the start of timing, all RO water in the RO water chamber 42 is discarded in step S5. Specifically, the RO water in the chamber is pushed out to the discard flow path with the positive pressure force by opening the electromagnetic valves 204 and 205 with the electromagnetic valves 206, 207, and 208 closed by the CPU 49a. The RO water accumulated in the RO water chamber 42 for a long time (eight hours) thus can be discarded. The RO water discarded from the RO water chamber 42 may again be transferred to the RO water producing unit 48, and new RO water may be produced from the discarded RO water. After all RO water in the RO water chamber 42 is discarded, the electromagnetic valves 204, 205, and 208 are closed and the electromagnetic valves 206 and 207 are opened by the CPU 49a in step S6, so that the RO water newly produced in the RO water producing unit 49 is supplied to the RO water chamber 42.

If at least one condition of the three conditions is not satisfied in step S1, the timing is reset in step S7, and the process returns to step S1.

The reagent preparation processing operation of the reagent preparing device 4 according to the first embodiment of the present invention will now be described with reference to FIGS. 6, 16, and 17.

The reagent preparation processing operation starts when the user instructs the activation of the device from the data processing section 3, that is, when the reagent preparing device 4 receives the activation signal from the data processing section 3. When the reagent preparation processing operation starts, initialization of the computer program stored in the ROM 49b is performed by the CPU 49a in step S11 of FIG. 16. In step S12, the CPU 49a determines whether or not the reagent preparing device 4 is normally shut down at the end of the previous operation. Specifically, determination is made based on a flag set to ON when normally shut down, as hereinafter described. The process proceeds to step S16 if normally shut down, and the process proceeds to step S13 if not normally shut down.

In step S13, the liquid in the chambers 42, 43, 44 and 46 other than the high concentration reagent chamber 41 and the supply chamber 47 are all discarded. Specifically, the electromagnetic valves 204 and 205 are opened with the electromagnetic valves 206, 207, and 208 closed by the CPU 49a to discard the RO water in the RO water chamber 42. The RO water discarded from the RO water chamber 42 may again be transferred to the RO water producing unit 48, and new RO water may be produced from the discarded RO water. Furthermore, the electromagnetic valves 218 and 221 are opened with the electromagnetic valves 211, 212, 217, and 219 closed by the CPU 49a to push out the mixed solution in the stirring chamber 46 to the discard flow path by the positive pressure force. The electromagnetic vales 211 and 217 are then opened with the electromagnetic valves 212, 218, 219, and 221 closed by the CPU 49a to transfer the mixed solution in the diluting chamber 43 to the stirring chamber 46 with the negative pressure force, and thereafter, the mixed solution is discarded from the stirring chamber 46 by the above-described operation. The mixed solution in the diluting chamber 44 also can be transferred to the stirring chamber 46 with the negative pressure force by opening the electromagnetic valves 212 and 217 with the electromagnetic valves 211, 218, 219, and 221 closed by the CPU 49a.

Therefore, the RO water having a possibility of being accumulated for a long time is prevented from being used in the reagent preparation, and the reagent of unknown diluting magnification is prevented from being prepared by discarding all liquids in the chambers 42, 43, 44, and 46 other than the high concentration reagent chamber 41 and the supply chamber 47 in step S13.

Since a high concentration reagent of the high concentration reagent chamber 41 contains an antiseptic agent, the quality of the high concentration reagent does not degrade with the accumulated time of about one month, and thus the high concentration reagent in the high concentration regent chamber 41 does not need to be discarded. Only the reagent diluted to the desired concentration is stored in the supply chamber 47, as hereinafter described, and the antiseptic agent contained in the high concentration reagent is mixed therein, and thus the reagent does not need to be discarded as the quality of the stored reagent does not have problems.

Thereafter, in step S14, the flow path, the RO water chamber 42, the diluting chamber 43 (44) and the stirring chamber 46 are cleaned. Specifically, about 12.0 mL (about 6.0 mL to each diaphragm pump) of RO water flows into the diaphragm pump 45a (45b) with the negative pressure force by opening the electromagnetic valves 206, 208, and 213 (215) by the CPU 49a after the RO water newly produced in the RO water producing unit 48 is supplied to the RO water chamber 42. The electromagnetic valves 214 (216) and 209 are then opened with the electromagnetic valves 208 and 213 (215) closed, so that about 12.0 mL (about 6.0 mL to each diaphragm pump) of RO water in the diaphragm pump 45a (45b) is transferred to the diluting chamber 43 with the positive pressure force. The above operations are repeated 25 times to supply about 300 mL of newly produced RO water to the diluting chamber 43.

About 300 mL of RO water is then transferred from the diluting chamber 43 to the stirring chamber 46 by opening the electromagnetic valves 211 and 217 by the CPU 49a. The RO water in the stirring chamber 46 is discarded by opening the electromagnetic valves 218 and 221 with the electromagnetic valves 217 and 219 closed by the CPU 49a.

While the RO water is being transferred from the diluting chamber 43 to the stirring chamber 46, about 300 mL of newly produced RO water is supplied to the diluting chamber 44 through the operation similar to the operation of transferring to the diluting chamber 43. The transfer of the RO water from the diluting chamber 44 to the stirring chamber 46 is also performed through the operation similar to the operation of transferring from the diluting chamber 43 to the stirring chamber 46. Therefore, the interior of the flow path, the RO water chamber 42, the diluting chamber 43 (44), and the stirring chamber 46 are cleaned with the newly produced RO water through the series of operations described above. A predetermined amount of RO water is already stored in the RO water chamber 42 through the operation similar to the RO water producing process of step S16, to be described later, before step S13.

In step S15, the reagent is prepared in the stirring chamber 46 through the operation similar to the operation of preparing the reagent of desired concentration, and all prepared reagent are discarded. Specifically, after the reagent of the desired concentration is supplied to the stirring chamber 46 by the operations of steps S21 and S22, described later, the reagent in the stirring chamber 46 is discarded by opening the electromagnetic valves 218 and 221 with the electromagnetic valves 217 and 219 closed by the CPU 49a. Thus, even if the reagent having a concentration exceeding the desired concentration remains in the flow path, the diluting chamber 43 (44) and the stirring chamber 46, the reagent can be suppressed from being prepared to the concentration other than the desired concentration since cleaning is carried out with the reagent of the desired concentration in addition to the cleaning by the RO water.

In step S16, the RO water producing process is performed in the RO water producing unit 48. The RO water production processing operation in step S16 of the reagent preparation processing operation shown in FIG. 16 will now be described with reference to FIGS. 6 and 18.

Figure 18:
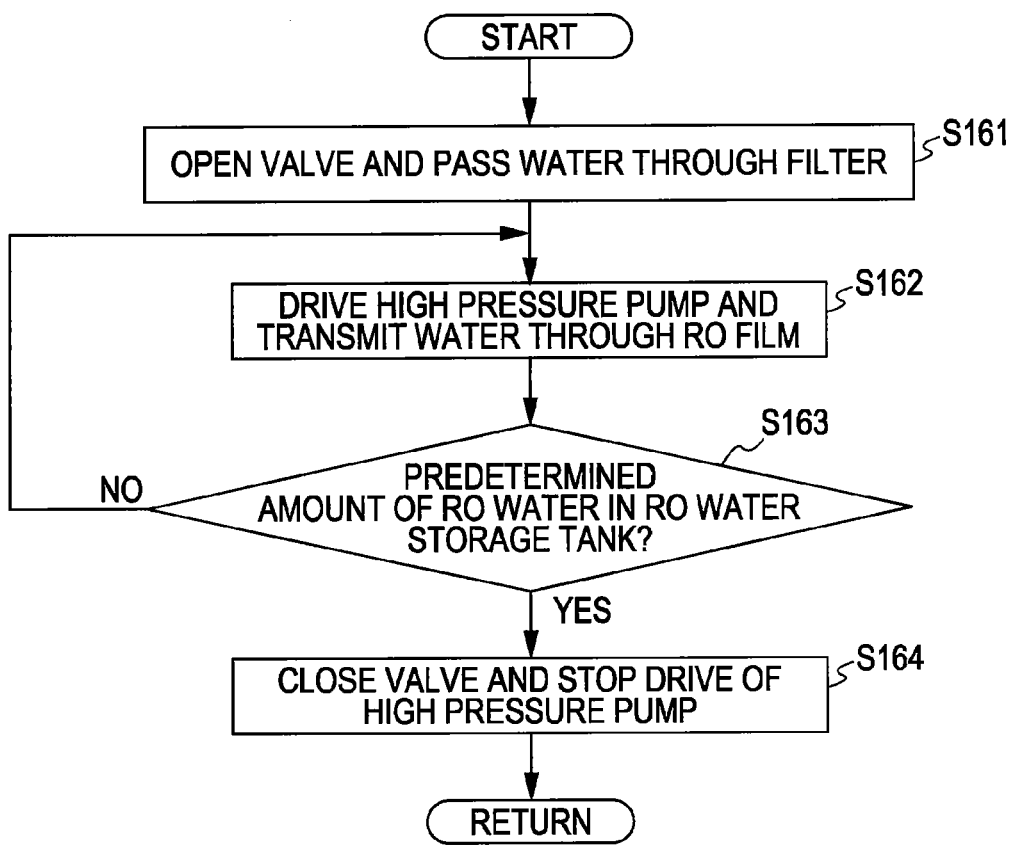
FIG. 18 is a flow chart explaining an RO water production processing operation in step S16 of the reagent preparation processing operation shown in FIG. 16.

First, in step S161 of FIG. 18, the electromagnetic valve 222 shown in FIG. 6 is opened by the CPU 49a and the tap water is passed through the filter 48c. In step S162, the high pressure pump 48d is driven by the CPU 49a, and the water passed through the filter 48c is transmitted through the RO film 48b by the high pressure. In step S163, whether or not a predetermined amount of RO water is accommodated in the RO water storage tank 48a is determined based on the detection result of the float switch 108. If the RO water is not the predetermined amount, the process returns to step S162, and the RO water is continuously supplied to the RO water storage tank 48a. If the RO water is the predetermined amount, the electromagnetic valve 222 is closed and the drive of the high pressure pump 48d is stopped in step S164 and the operation is terminated.

Figure 16:
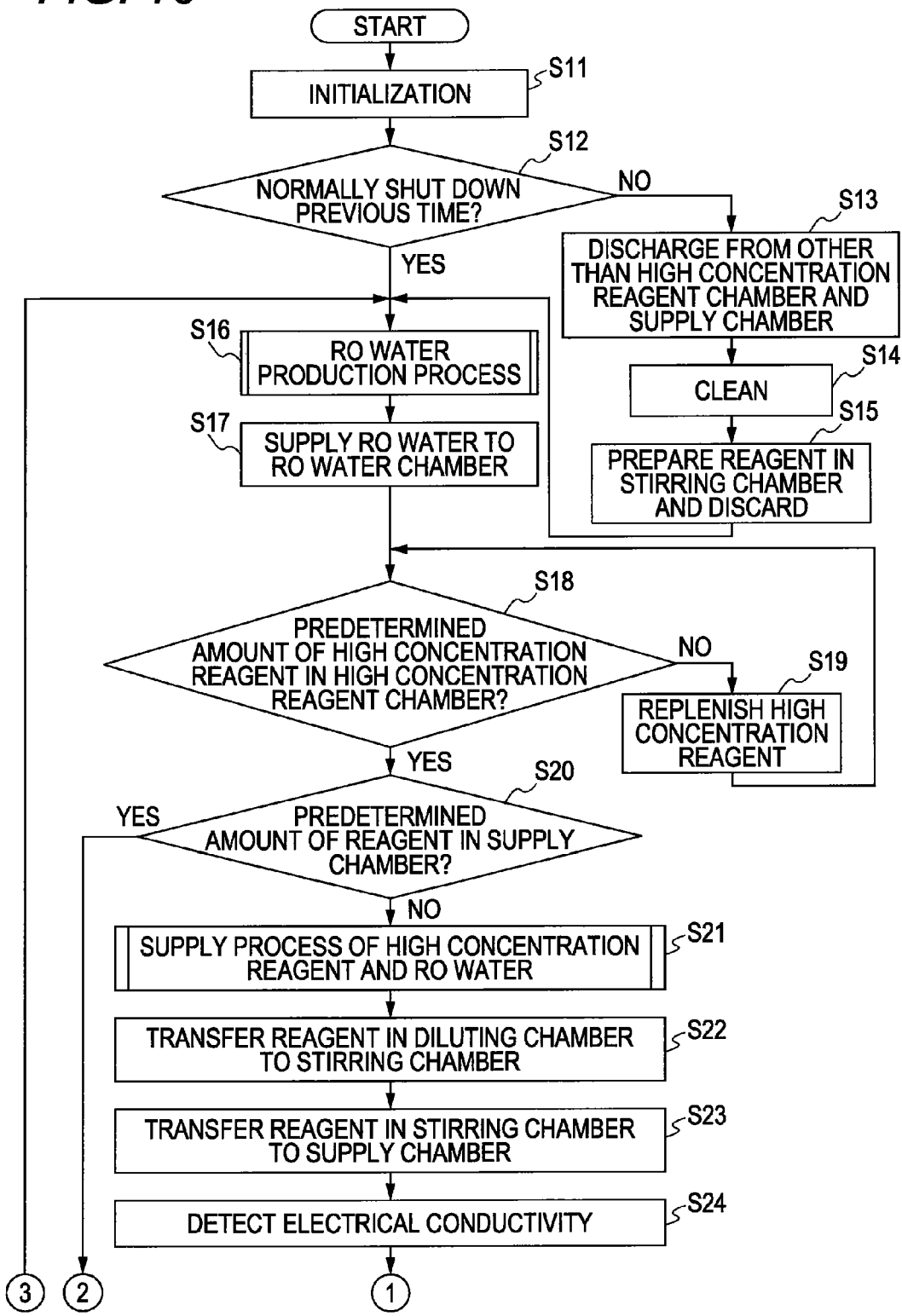
FIG. 16 is a flowchart explaining a reagent preparation processing operation of the reagent preparing device according to the first embodiment of the present invention.
Figure 17:
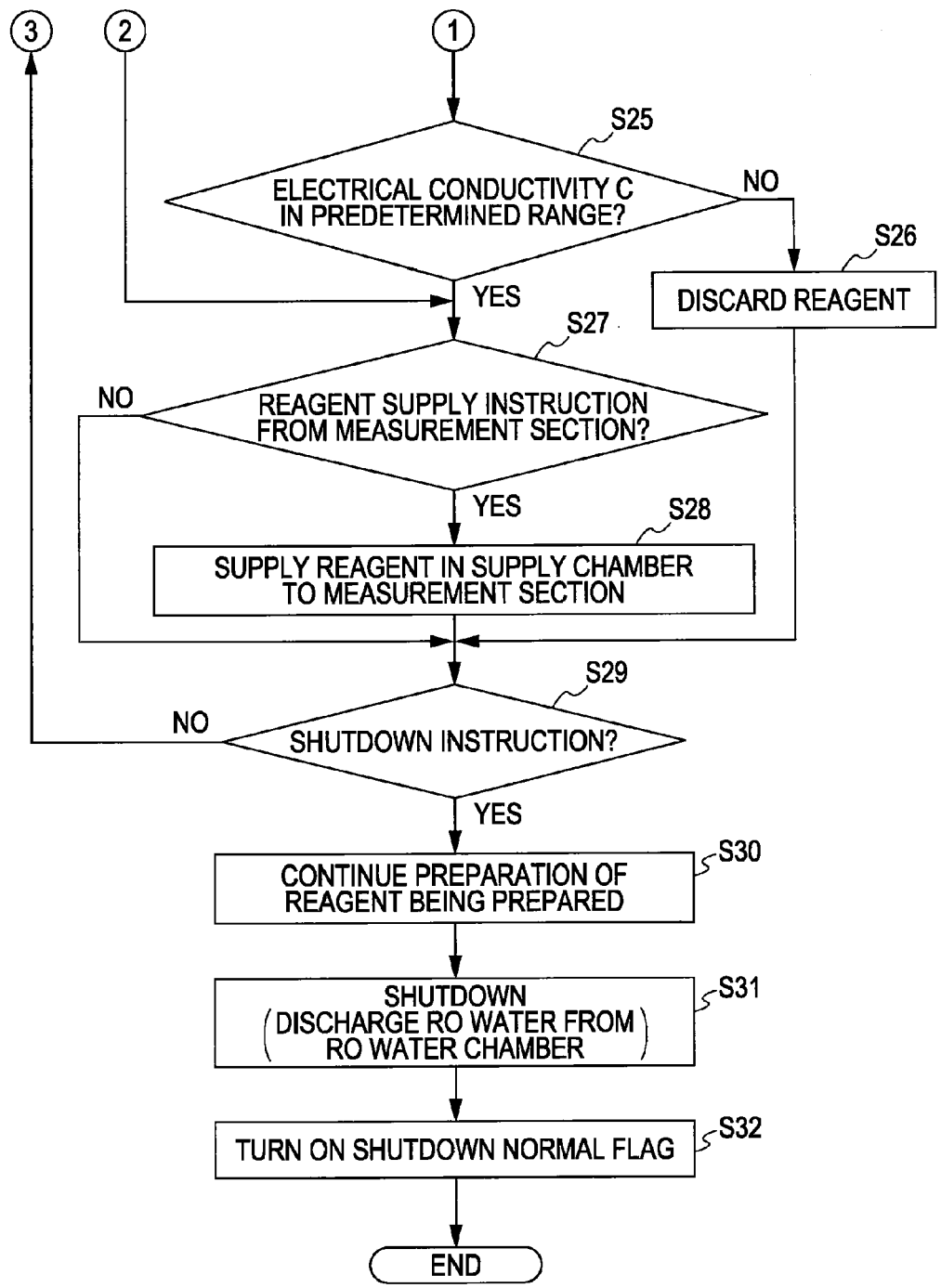
FIG. 17 is a flowchart explaining the reagent preparation processing operation of the reagent preparing device according to the first embodiment of the present invention.

After the RO water production processing operation of step S16 of FIG. 16 is terminated, the RO water is supplied to the RO water chamber 42 in step S17. In step S18, whether or not a predetermined amount of high concentration reagent is accommodated in the high concentration reagent chamber 41 is determined based on the detection result of the float switch 100 by the CPU 49a. If the predetermined amount of high concentration reagent is not stored, the high concentration reagent is replenished to the high concentration reagent chamber 41 from the high concentration reagent tank 5 in step S19. Specifically, the electromagnetic valves 200 and 201 are opened with the electromagnetic valves 202 and 203 closed by the CPU 49a, so that the high concentration reagent is supplied to the high concentration reagent chamber 41 with the negative pressure force.

If the predetermined amount of high concentration reagent is accommodated in the high concentration reagent chamber 41, whether or not the predetermined amount of reagent is stored in the supply chamber 47 is determined by the CPU 49*a*. In other words, whether or not the reagent of greater than or equal to about 300 mL and less than or equal to about 600 mL is stored in the supply chamber 47 is determined. The process proceeds to step S27 if the predetermined amount of reagent is stored. If the predetermined amount of reagent is not stored, the supply process of the high concentration reagent and the RO water is performed in step S21.

The supply processing operation of the high concentration reagent and the RO water in step S21 of the reagent preparation processing operation shown in FIG. 16 will be described with reference to FIGS. 6, 12, 13, and 19.

First, in the initial state (state immediately before reagent preparation process) of the reagent preparing device 4, the flow paths 301 to 304 shown in FIG. 6 are substantially filled with RO water and the flow path 300 is substantially filled with high concentration reagent. The flow path 300 and the flow path 301 are directly connected, but the high concentration reagent in the flow path 300 is difficult to be mixed with the RO water in the flow path 301 since the inner diameter of the flow path 301 is about 4.0 mm and the inner diameter of the flow path 300 (300*a*) is small or about 1.8 mm. The flow path 300*a* between the electromagnetic valve 203 and the flow path 301 is set such that the inner diameter is about 1.8 mm and the length is small or about 15 mm, and thus the amount of high concentration reagent in the flow path 300*a* is very small.

Figure 19:
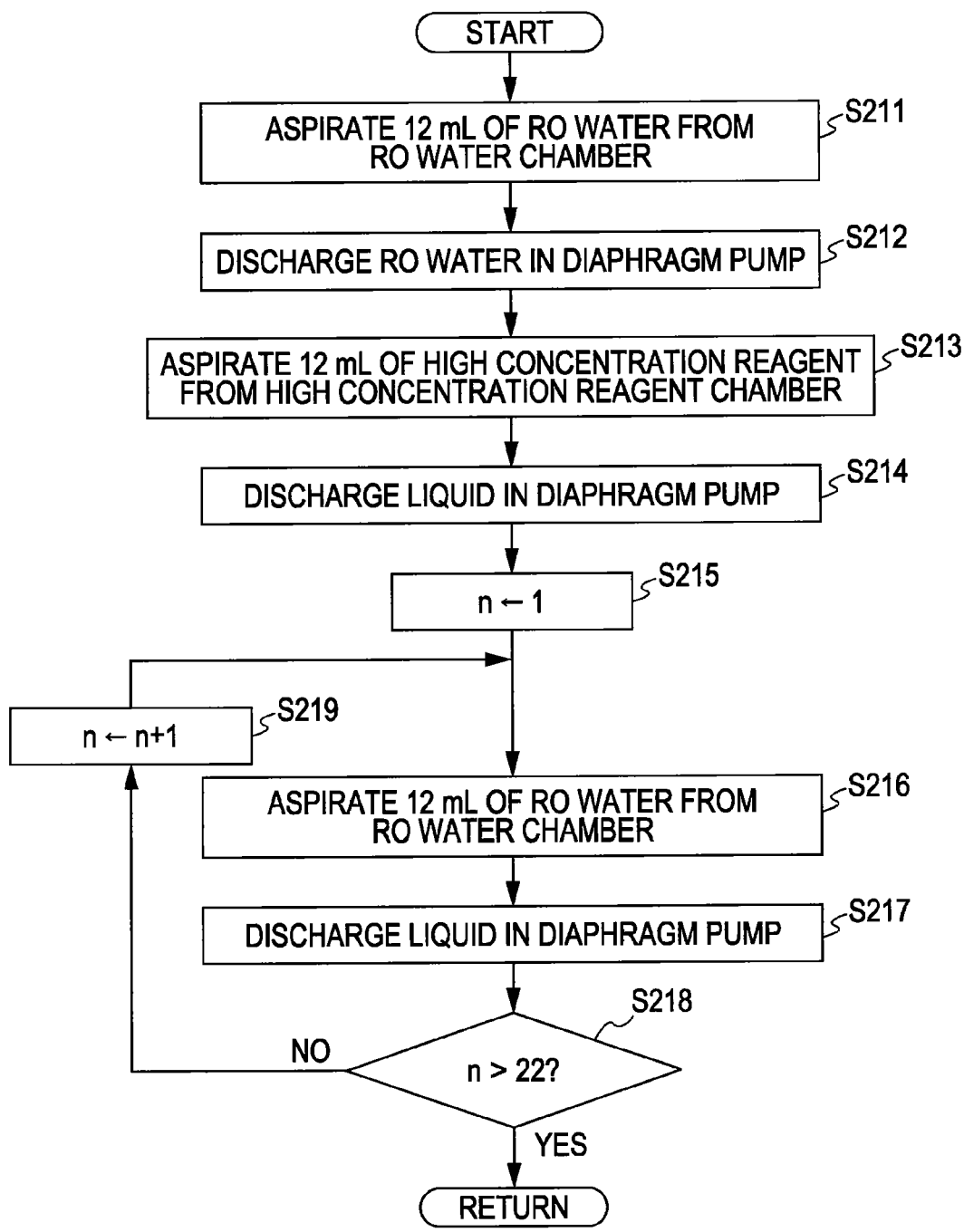
FIG. 19 is a flowchart explaining a supply processing operation of a high concentration reagent and RO water in step S21 of the reagent preparation processing operation shown in FIG. 16.

In step S211 of FIG. 19, about 12.0 mL (about 6.0 mL in each diaphragm pump) of RO water is aspirated from the RO water chamber 42 by the diaphragm pumps 45*a* and 45*b*. Specifically, the electromagnetic valves 213 (215) and 208 are opened by the CPU 49*a*, so that the negative pressure is supplied to the chamber portion 452*f* and the RO water flows into the chamber portion 453*f* through the flow path 302, as shown in FIG. 12. In step S212, the electromagnetic valves 214 (216) and 209 are opened after the electromagnetic valves 213 (215) and 208 are closed, so that positive pressure is supplied to the chamber portion 452*f* and RO water is discharged from the chamber portion 453*f*, as shown in FIG. 13. Thus, about 12.0 mL (about 6.0 mL in each diaphragm pump) of RO water is supplied to the diluting chamber 43 through the flow paths 301 and 303.

Thereafter, in step S213, about 12.0 mL (about 6.0 mL in each diaphragm pump) of high concentration reagent is aspirated from the high concentration reagent chamber 41 by the diaphragm pumps 45*a* and 45*b*. Specifically, the electromagnetic valves 202, 203, and 213 (215) are opened after the electromagnetic valves 214 (216) and 209 are closed by the CPU 49*a*, so that the negative pressure is supplied to the chamber portion 452*f* and the high concentration reagent is aspirated to the chamber portion 453*f* through the flow paths 300 and 301, as shown in FIG. 12. Specifically, about 12.0 mL of high concentration reagent flowed out from the high concentration reagent chamber 41 mixes with the RO water remaining in the flow path 301, and the mixed solution of the RO water and the high concentration reagent is aspirated to the chamber portion 453*f*. The mixed solution of the RO water and the high concentration reagent is filled in the flow path 301 in this case. In other words, about 12.0 mL of high concentration reagent flowed out from the high concentration reagent chamber 41 exists in a region combining the chamber portion 453*f* and the flow path 301 in this state. The high concentration reagent also exists in the flow path 300*a*, but can be substantially ignored as the amount of high concentration reagent existing in the flow path 300*a* is very small. Furthermore, at the time of aspirating the high concentration reagent after the second reagent preparation processing operation, the high concentration reagent remaining in the flow path 300*a* from the previous reagent preparation processing operation is pushed out to the flow path 301 side, and thus about 12.0 mL of high concentration reagent more accurately exists in the region combining the chamber portion 453*f* and the flow path 301.

In step S214, the electromagnetic valves 214 (216) and 209 are opened after the electromagnetic valves 202, 203, and 213 (215) are closed, so that positive pressure is supplied to the chamber portion 452*f* and the mixed solution of RO water and high concentration reagent is discharged from the chamber portion 453*f*, as shown in FIG. 13. Thus, the mixed solution of RO water and high concentration reagent is supplied to the diluting chamber 43 through the flow paths 301 and 303. In this case, a few mL of high concentration reagent remains mixed with the RO water in the flow paths 301 and 303.

In step S215, n=1 is set by the CPU 49*a*. Here, n is the number of discharging of the RO water by the diaphragm pumps 45*a* and 45*b*, and is defined with a real number starting from 1. In step S216, about 12.0 mL of RO water is aspirated from the RO water chamber 42 by the diaphragm pumps 45*a* and 45*b*, similar to step S211. Similar to step S212, in step S217, the RO water is discharged from the chamber portion 453*f* of the diaphragm pumps 45*a* and 45*b*. Thus, the high concentration reagent remaining in the flow paths 301 and 303 is transferred to the diluting chamber 43 with the RO water.

Thereafter, in step S218, whether or not n is greater than 22 is determined by the CPU 49*a*. If n is not greater than 22, n=n+1 is set in step S219, and the operations of steps S216 to S219 are repeated until n is greater than 22. In other words, the operations of steps S216 to S219 are repeated until the aspiration and discharge operation of the RO water are performed 24 times with respect to one aspiration and discharge operation of the high concentration reagent by the diaphragm pumps 45*a* and 45*b*. The operation is terminated when n is greater than 22. Thus, about 12.0 mL×24 times=about 288 mL of RO water and about 12.0 mL×1 time=about 12 mL of high concentration reagent, that is, the mixed solution of about 288 mL+about 12 mL=about 300 mL is supplied to the diluting chamber 43. After the aspiration and discharge operation of the high concentration reagent by the diaphragm pumps 45*a* and 45*b*, the aspiration and discharge operation of the RO Water is performed 23 times, and thus the high concentration reagent remaining in the flow paths 301 and 303 are all transferred to the diluting chamber 43, and only the RO water consequently exists in the flow paths 301 and 303.

In the above operation, if the electromagnetic valve 210 is driven in place of the electromagnetic valve 209, about 300 mL of mixed solution containing about 288 mL of RO water and about 12 mL of high concentration reagent can be transferred to the diluting chamber 44.

After the supply process of the high concentration reagent and the RO water is performed by step S21 of FIG. 16, the electromagnetic valves 211 (212) and 217 are opened by the CPU 49*a* to transfer the reagent in the diluting chamber 43 (44) to the stirring chamber 46 with the negative pressure force in step S22. In this case, the transferred reagent is flowed along the inner wall of the stirring chamber 46 by the pipe 416 arranged in the stirring chamber 46 so as to be stirred in the stirring chamber 46.

In step S23, the electromagnetic valves 218 and 219 are opened after the electromagnetic valves 211 (212) and 217 are closed, and the reagent is transferred from the stirring chamber 46 to the supply chamber 47. In step S24, the electrical conductivity C is measured by the conductivity sensor 402 and the temperature T2 of the reagent is measured by the temperature sensor 403. In step S25, whether or not the electrical conductivity C is within a predetermined range is determined by the CPU 49a. Specifically, whether or not the measured electrical conductivity C is within the predetermined range is determined with respect to the target value Z of the electrical conductivity at the diluting magnification of 25 times calculated by equation (2). If the electrical conductivity C is not within the predetermined range, the electromagnetic valve 219 is closed and the electromagnetic valve 221 is opened, and the reagent in which the electrical conductivity C is not within the predetermined range is discarded through the discard flow path in step S26. Only the reagent diluted at satisfactory accuracy thus can be stored in the supply chamber 47.

In step S27, whether or not the reagent supply instruction from the measurement section 2 transmitted through the data processing section 3 is made is determined by the CPU 49a, and the process proceeds to step S29 if instruction is not made. If the reagent supply instruction is made, the reagent in the supply chamber 47 is transferred to the measurement section 2 through the filter 471 by the negative pressure force supplied from the measurement section 2 in step S28. In step S29, the presence of shutdown instruction from the user is determined by the CPU 49a, and the process proceeds to step S16 if the instruction is not made.

If the shutdown instruction is made, the above operation is continued until the reagent in the middle of the preparation is ultimately transferred to the supply chamber 47 in step S30. Specifically, if a predetermined amount (greater than or equal to about 300 mL and less than or equal to about 600 mL) of reagent is not in the supply chamber 47, the reagent diluted to a concentration different from the desired concentration remains in the flow path, the diluting chamber 43 (44), and the stirring chamber 46 when the operation is stopped in the middle of the preparation since the reagent preparation is continued through the operations of steps S21 to S26. Thus, the reagent diluted to a concentration different from the desired concentration is prevented from remaining in the flow path, the diluting chamber 43 (44), and the stirring chamber 46 by continuing the preparation operation in step S30.

In step S31, the shutdown is executed. In this case, the RO water is discharged from the RO water chamber 42. The RO water is thus prevented from being accumulated in the RO water chamber 42 until the reagent preparing device 4 is activated at the next time. Thereafter, in step S32, the flag indicating that the shutdown has been normally performed is set to ON, and the reagent preparation processing operation is terminated. The reagent preparation process shown in FIGS. 16 and 17, and the RO water automatic discharge process shown in FIG. 15 are continuously executed in parallel while the reagent preparing device 4 is operating by the CPU 49a.

In the first embodiment, the reagent can be rapidly prepared using the RO water stored in advance when the necessity to supply the reagent arises since the RO water chamber 42 for storing the RO water is arranged and the RO water can be stored in advance in the RO water chamber 42. Furthermore, in the reagent preparing device 4, the RO water is prevented from being accumulated in the RO water chamber 42 over eight hours by discarding the RO water stored in the RO water chamber 42 when the timed accumulated time reaches eight hours by the CPU 49a, and thus degradation in the quality of the RO water caused by generation of bacteria in the RO water, and the like can be suppressed. Thus, the reagent with degraded quality caused by using the RO water with degraded quality is suppressed from being prepared. Therefore, in the reagent preparing device 4, the reagent can be rapidly prepared and the reagent with degraded quality is suppressed from being prepared.

Furthermore, in the first embodiment, the CPU 49a is configured to start timing when the RO water stops being used, so that the time from when the RO water starts to accumulate in the RO water chamber 42 can be timed, and the accumulated time of the RO water in the RO water chamber 42 can be more accurately timed.

In the first embodiment, the RO water is resupplied to the RO water chamber 42 when the RO water stored in the RO water chamber 42 is discarded by the CPU 49a, so that the RO water can be resupplied to the RO water chamber 42 even when the RO water is discarded from the RO water chamber 42, and the next reagent preparation process can be rapidly performed using the resupplied RO water.

Moreover, in the first embodiment, the CPU 49a is configured to determine whether or not the operation is normally terminated at the end of the previous operation, and discard the RO water stored in the RO water chamber 42 and resupply the RO water to the RO water chamber 42 where the RO water has been discarded when determined that the operation is not terminated normally, so that the RO water in the RO water chamber 42 is discarded even when the RO water is accumulated for a long time in the RO water chamber 42 as the operation is not normally terminated at the end of the previous operation, and the RO water having a possibility of being degraded due to accumulation of a long time is prevented from being used for the reagent preparation. Furthermore, since the RO water is resupplied to the RO water chamber after the accumulated RO water is discarded, the next reagent preparation process can be rapidly performed using the resupplied RO water.

In the first embodiment, when determined that the operation of the reagent preparing device 4 is not normally terminated by the CPU 49a, the mixed solution stored in the diluting chamber 43 (44) and the stirring chamber 46 is discarded so that the mixed solution having a possibility of being mixed at a concentration different from the desired concentration in the diluting chamber 43 (44) and the stirring chamber 46 as the operation is not normally terminated at the end of the previous operation is discarded, and the reagent of a concentration other than the desired concentration is prevented from being supplied to the measurement section 2.

In the first embodiment, the RO water stored in the RO water chamber 42 is discarded after the shutdown instruction of the reagent preparing device 4 is accepted by the CPU 49a, so that the RO water is prevented from being accumulated in the RO water chamber 42 after the reagent preparing device 4 is shut down until the operation is resumed.

Second Embodiment

A second embodiment will be described with reference to FIGS. 20 and 21. In the second embodiment, a reagent preparing device 600 in which the RO water producing unit 700 is arranged at the exterior, different from the first embodiment, will be described.

Figure 20:
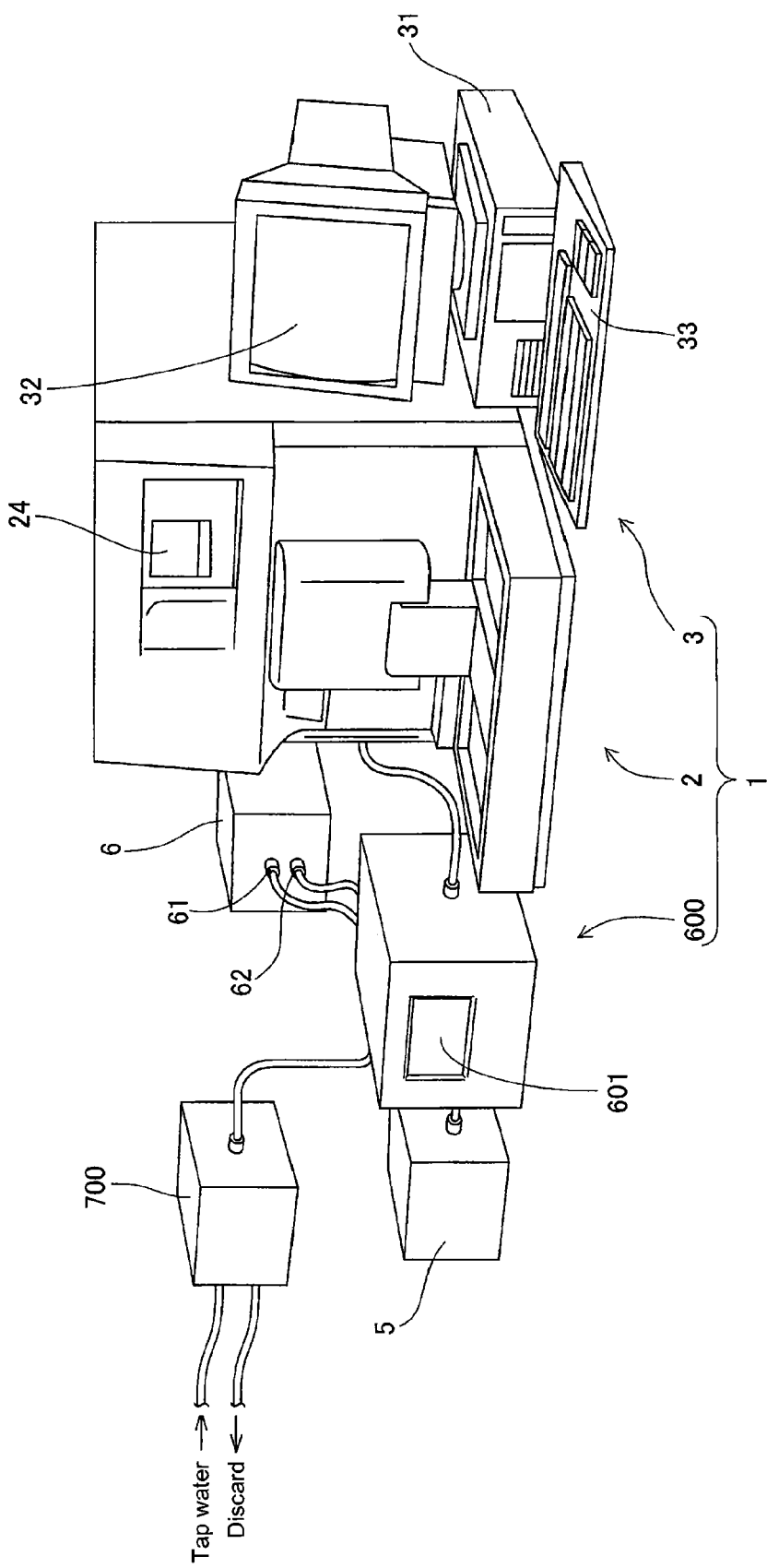
FIG. 20 is a perspective view showing a usage mode of a reagent preparing device according to a second embodiment of the present invention.

As shown in FIG. 20, the blood analyzer 1 is configured by the measurement section 2 having a function of measuring blood, the data processing section 3 for analyzing the measurement data output from the measurement section 2 and obtaining an analysis result, and the reagent preparing device 600 for preparing a reagent to be used in the processing of specimens.

Figure 21:
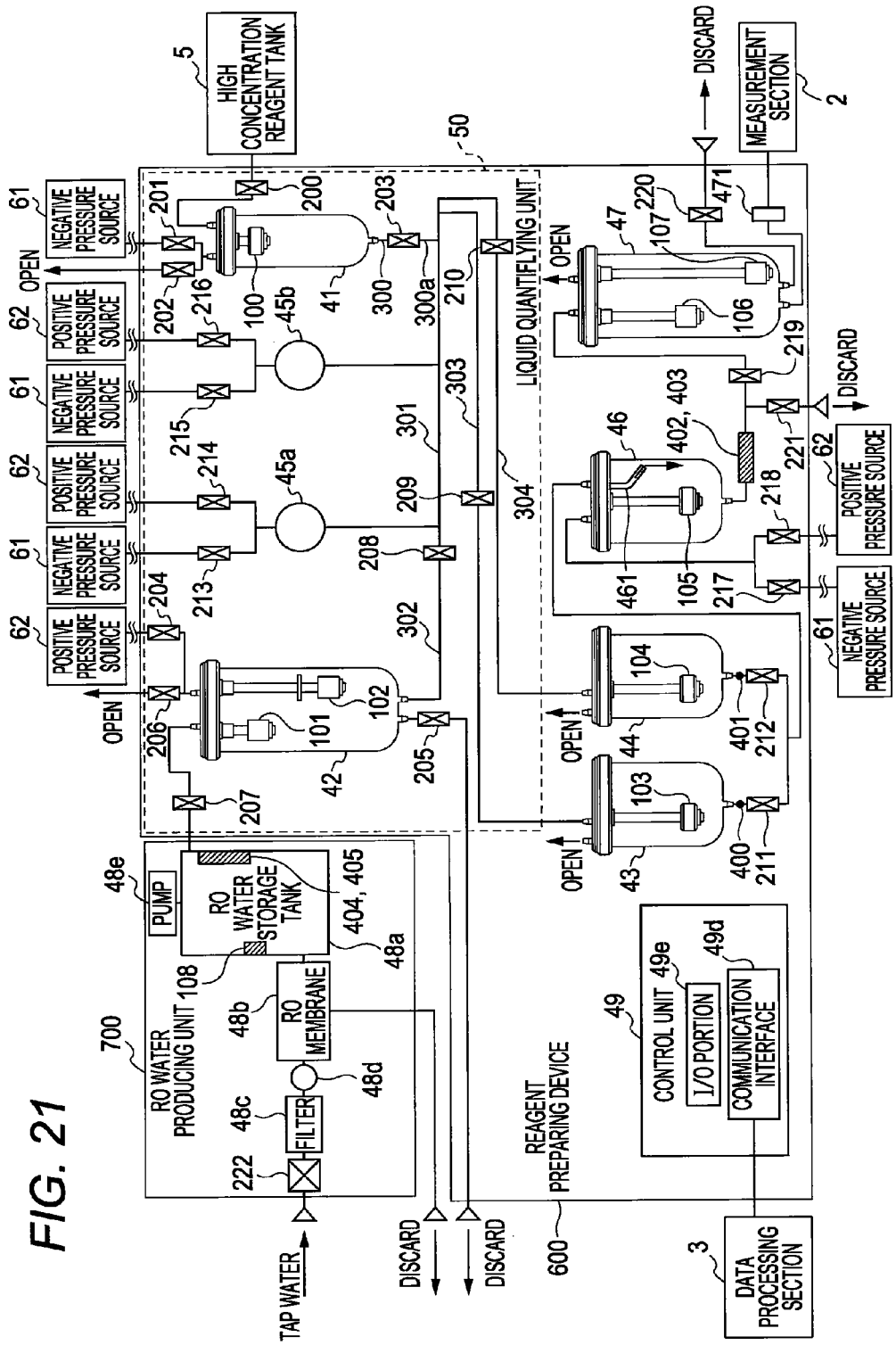
FIG. 21 is a block diagram showing a configuration of the reagent preparing device according to the second embodiment shown in FIG. 20.

As shown in FIGS. 20 and 21, in the second embodiment, the reagent preparing device 600 is configured to prepare the reagent to be used in blood analysis by diluting the high concentration reagent to a desired concentration using the RO water produced by the RO water producing unit 700 arranged at the exterior.

As shown in FIG. 20, the reagent preparing device 600 includes a touch panel type display unit 601. The CPU 49a of the reagent preparing device 600 is configured to accept instructions such as activation of the reagent preparing device 600, shutdown, and various types of settings from the user through the touch panel type display unit 601.

Other structures of the second embodiment are similar to those of the first embodiment.

In the second embodiment, the configuration of the reagent preparing device 600 is simplified by arranging the RO water producing unit 700 at the exterior of the reagent preparing device 600.

Other effects of the second embodiment are similar to the first embodiment.

The embodiments disclosed herein are illustrative in all aspects and should not be construed as being exclusive. The scope of the present invention is defined by the Claims rather than by the description of the embodiments made above, and all modifications equivalent in meaning to the Claims and within the scope of the Claims are to be encompassed.

For instance, an example of diluting the high concentration reagent to 25 times has been described in the first embodiment and the second embodiment, but the present invention is not limited thereto, and the high concentration reagent may be diluted to magnifications other than 25 times such as 20 times. In this case, after quantifying the RO water once using the diaphragm pumps 45a and 45b, the high concentration reagent is quantified once, and then the RO water is quantified 18 times to prepare the reagent having a diluting magnification of 20 times.

In the first embodiment and the second embodiment, an example in which after the RO water serving as the diluting liquid is quantified once, the high concentration reagent is quantified once, and then the RO water is quantified 23 times to prepare the reagent having a diluting magnification of 25 times has been described, but the present invention is not limited thereto, and after the RO water is quantified twice, the high concentration reagent may be quantified once and then the RO water may be quantified 22 times to prepare a reagent having a diluting magnification of 25 times.

In the first embodiment and the second embodiment, an example in which two diaphragm pumps 45a and 45b are arranged has been described, but the present invention is not limited thereto, and one diaphragm pump may be arranged, or two or more diaphragm pumps may be arranged.

Furthermore, in the first embodiment and the second embodiment, an example in which the diaphragm pump is commonly used both to transfer the RO water and to transfer the high concentration reagent has been described, but the present invention is not limited thereto, and a plurality of diaphragm pumps may be arranged, and the transfer of the RO water and the transfer of the high concentration reagent may be carried out using different diaphragm pumps.

In the first embodiment and the second embodiment, an example of quantifying the RO water and the high concentration reagent using the diaphragm pump has been described, but the present invention is not limited thereto, and the RO water and the high concentration reagent may be quantified using a syringe pump in which the amount of stroke of the piston is fixed as long as it is a quantifier that can quantify a constant amount of liquid defined in advance in one quantifying operation.

Figure 22:
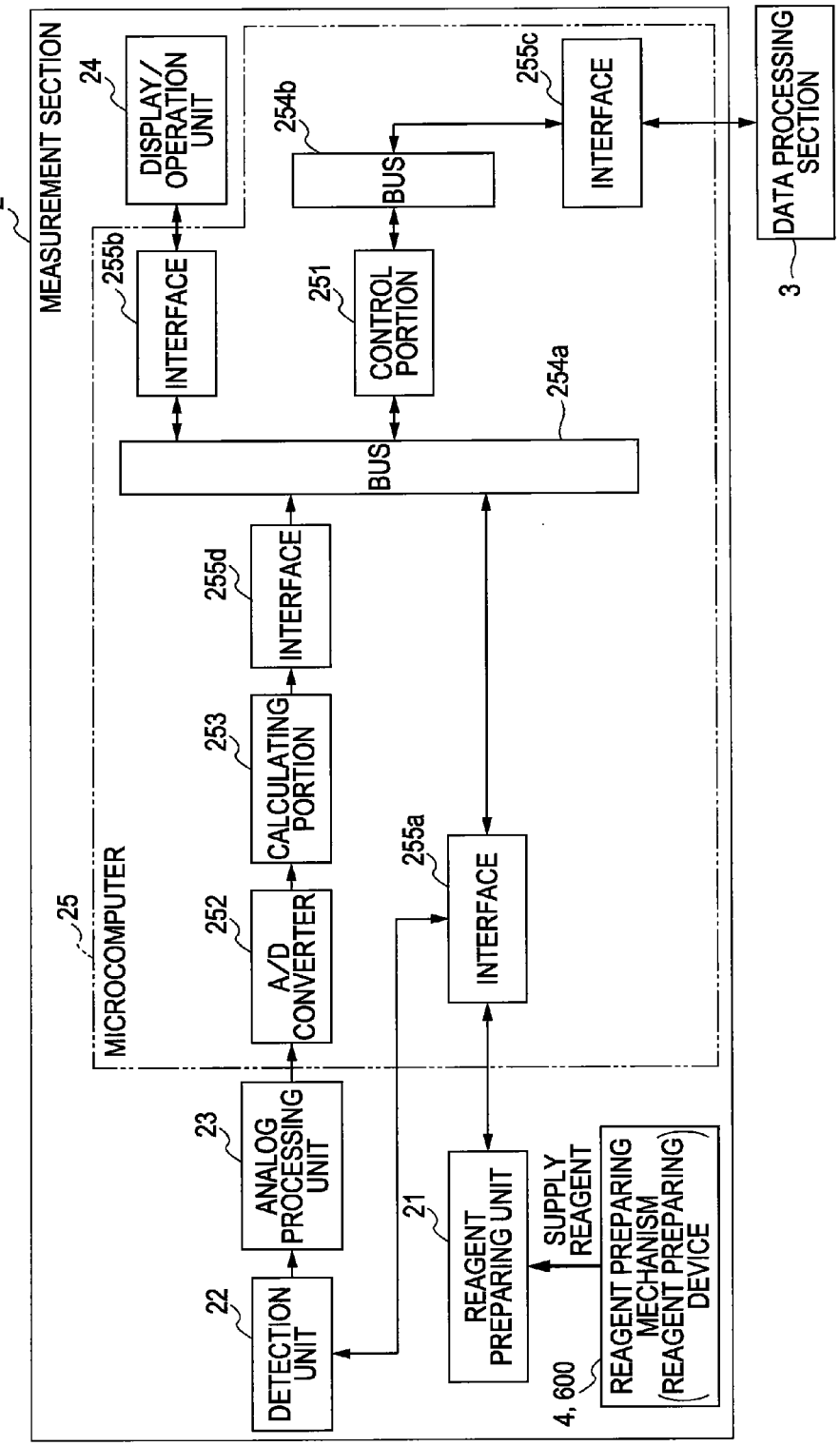
FIG. 22 is a block diagram explaining a variant of the reagent preparing device according to the first embodiment shown in FIG. 1 and the second embodiment shown in FIG. 20.

In the first embodiment and the second embodiment, the reagent preparing device installed separate from the measurement section has been described as one example of the reagent preparing device, but the present invention is not limited thereto, and it may be a reagent preparing device arranged in the measurement section and having a function of a reagent preparing mechanism, as shown in FIG. 22. The measurement section (device) equipped with the reagent preparing mechanism includes blood cell counting device, immune measurement device, and smear producing device, but is particularly suited to the blood cell counting device in which the usage amount of the diluting liquid is large.

In the first embodiment and the second embodiment, an example of discarding the RO water when the RO water is accumulated in the RO water chamber for eight hours has been described, but the present invention is not limited thereto, and the RO water may be discarded in a time shorter than eight hours or the RO water may be discarded in a time longer than eight hours as long as it is a time in a range the quality of the RO water does not degrade.

What is claimed is:

1. A reagent preparing device for preparing a reagent to be supplied to a measurement device for measuring a specimen, comprising:
    water containing no antiseptic agent;
    a concentrated reagent containing an antiseptic agent;
    a supply chamber for storing the reagent, including the water containing no antiseptic agent and a containing the concentrated reagent antiseptic agent, to be supplied to the measurement device;
    a diluting chamber for preparing the reagent by diluting the concentrated reagent with the water and for supplying the reagent to the supply chamber, wherein the supply chamber and the diluting chamber are connected;
    a water chamber for storing the water containing no antiseptic agent and for supplying the water to the diluting chamber;
    a concentrated reagent chamber for storing the concentrated reagent and for supplying the concentrated reagent to the diluting chamber;
    a water discarding unit for discarding the water stored in the water chamber; and
    a processor programmed to:
    measure an accumulated time of the water in the water chamber;
    and control the water discarding unit to discard the water stored in the water chamber without discarding the reagent in the supply chamber when the accumulated time reaches a predetermined time,
    wherein the processor starts measurement of the accumulated time when the water in the water chamber is not supplied to the diluting chamber and
    the processor controls the water discarding unit to discard the water stored in the water chamber without discarding the reagent in the supply chamber when accepting an instruction to shutdown operation of the reagent preparing device.

2. The reagent preparing device according to claim 1, wherein the water chamber is configured to store pure water as the water.

3. The reagent preparing device according to claim 1, wherein the processor starts measurement of the accumulated time when the water in the water chamber starts accumulating in the water chamber instead of being supplied to the diluting chamber, and absent a supply of the water from the water chamber, no reagent is prepared in the dilution chamber.

4. The reagent preparing device according to claim 3, wherein the processor determines, based on an amount of the reagent stored in the reagent storage unit, whether the water in the water chamber should not supplied to the diluting chamber, and absent a supply of the water from the water chamber, no reagent is prepared in the dilution chamber.

5. The reagent preparing device according to claim 1, further comprising:
   a water producing unit for producing the water to be supplied to the water chamber, wherein
   the processor controls the water producing unit to produce the water to be resupplied to the water chamber after discarding the water stored in the water chamber is completed.

6. The reagent preparing device according to claim 1, further comprising:
   a water producing unit for producing the water to be supplied to the water chamber, wherein
   the processor controls the water producing unit to produce the water to be supplied to the water chamber when accepting an instruction to activate the reagent preparing device.

7. The reagent preparing device according to claim 6, wherein the processor
   determines whether a previous termination process of the reagent preparing device is normal when accepting the instruction to activate the reagent preparing device; and
   controls, when determined that the termination process is not normal, the water discarding unit and the water producing unit to discard the water stored in the water chamber, and to produce the water to be resupplied to the water chamber, in which the water is discarded.

8. The reagent preparing device according to claim 1, further comprising:
   a pneumatic unit for generating pressure for transferring the water and the concentrated reagent, wherein
   the reagent is prepared by transferring the water and the concentrated reagent by the pressure generated by the pneumatic unit.

9. The reagent preparing device according to claim 8, wherein the water discarding unit comprises,
   a discard flow path for discarding the water from the water chamber, and
   a first valve for opening and closing the discard flow path, wherein
   the processor controls the opening and closing operation of the first valve.

10. The reagent preparing device according to claim 8, further comprising:
    a flow path for connecting the water chamber and the diluting chamber; and
    a second valve for opening and closing the connection flow path, wherein
    the processor controls the opening and closing operation of the second valve to prepare the reagent.

11. The reagent preparing device according to claim 1, wherein the processor continues to prepare the reagent in the diluting chamber even if the instruction to shutdown operation is accepted during the preparation of the reagent, and
    the processor controls the water discarding unit to discard the water stored in the water chamber without discarding the reagent in the supply chamber after the preparation of the reagent is completed.

12. The reagent preparing device according to claim 1, further comprising a conductivity sensor provided in a flow path between the supply chamber and the diluting chamber, wherein
    the processor controls the reagent stored in the diluting chamber to flow in the flow path and controls the conductivity sensor to measure a conductivity of the reagent, and
    the processor controls the water discarding unit to discard the reagent if the conductivity of the reagent does not meet a predetermined condition.

13. A specimen measuring device comprising:
    water containing no antiseptic agent;
    a concentrated reagent containing an antiseptic agent;
    a measurement section for measuring a specimen using a reagent including the water containing no antiseptic agent and the concentrated reagent containing an antiseptic agent; and
    a reagent preparing unit comprising:
       a supply chamber for storing the reagent to be supplied to the measurement section,
       a diluting chamber for preparing the reagent by diluting the concentrated reagent with the water and for supplying the reagent to the supply chamber,
       a water chamber for storing the water and for supplying the water to the diluting chamber,
       a concentrated reagent chamber for storing the concentrated reagent and for supplying the concentrated reagent to the diluting chamber,
       a water discarding unit for discarding the water stored in the water chamber; and
    a processor programmed to:
       measure an accumulated time of the water in the water chamber, and
       control the water discarding unit to discard the water stored in the water chamber without discarding the reagent in the supply chamber when the accumulated time reaches a predetermined time, wherein
    the processor starts measurement of the accumulated time when the water in the water chamber is not supplied to the diluting chamber,
    the processor controls the water discarding unit to discard the water stored in the water chamber without discarding the reagent in the supply chamber when accepting an instruction to shutdown operation of the reagent preparing unit.

14. The specimen measuring device according to claim 13, wherein
    the specimen is blood; and
    the measurement section dilutes the blood with the reagent prepared by the reagent preparing unit, and counts the blood cells in the blood.

15. The specimen measuring device according to claim 14, wherein the measurement section further uses the reagent prepared by the reagent preparing unit as a cleaning fluid.

16. A reagent preparing method for preparing a reagent to be supplied to a measurement device for measuring a specimen, comprising:
    supplying water containing no antiseptic agent to a water chamber;
    supplying the water in the water chamber to the diluting chamber;
    supplying a concentrated reagent containing an antiseptic agent to the diluting chamber;
    preparing a reagent including the water containing no antiseptic agent and the concentrated reagent containing an antiseptic agent by diluting the concentrated reagent with the water in the diluting chamber;

supplying the reagent in the diluting chamber to a supply chamber for storing the reagent to be supplied to the measurement device;

measuring with a processor an accumulated time of the water in the water chamber;

discarding the water stored in the water chamber without discarding the reagent in the supply chamber when the accumulated time reaches a predetermined time, discarding the water stored in the water chamber without discarding the reagent in the supply chamber when accepting an instruction to shutdown, and wherein measuring the accumulated time comprises starting measurement of the accumulated time with the processor when the water in the liquid water chamber is not supplied to the diluting chamber.

17. The reagent preparing device according to claim 1, wherein the processor resets the accumulated time when a supply of the water in the water chamber to the diluting chamber is started.

* * * * *